United States Patent [19]

Levitt et al.

[11] Patent Number: 4,655,821
[45] Date of Patent: Apr. 7, 1987

[54] ALKYL SULFONYL SULFONAMIDES

[75] Inventors: George Levitt, Wilmington, Del.; Anthony D. Wolf, Elkton, Md.

[73] Assignee: E. I. Du Pont de Nemours and Company, Wilmington, Del.

[21] Appl. No.: 754,141

[22] Filed: Jul. 12, 1985

Related U.S. Application Data

[60] Division of Ser. No. 511,471, Jul. 8, 1983, Pat. No. 4,543,120, which is a continuation-in-part of Ser. No. 407,645, Aug. 12, 1982, abandoned.

[51] Int. Cl.$^4$ ............... C07D 239/42; C07D 239/48; A01N 47/36

[52] U.S. Cl. ......................................... 71/92; 544/321; 544/323; 544/332

[58] Field of Search .................... 71/92; 544/321, 332, 544/323

[56] References Cited

FOREIGN PATENT DOCUMENTS 35893 9/1981 European Pat. Off. ................ 71/90

Primary Examiner—Robert Gerstl

[57] ABSTRACT

This invention relates to alkyl sulfonyl sulfonamides which are useful as herbicides and plant growth regulants.

19 Claims, No Drawings

ALKYL SULFONYL SULFONAMIDES

RELATED APPLICATION

This is a division of application Ser. No. 511,471, filed July 8, 1983, now U.S. Pat. No. 4,543,120 which is in turn a continuation-in-part of my copending application U.S. Ser. No. 407,645, filed Aug. 12, 1982 now abandoned.

BACKGROUND OF THE INVENTION

This invention relates to novel alkyl sulfonyl sulfonamides. The compounds of this invention and their agriculturally suitable salts, are useful as agricultural chemicals, e.g. plant growth regulators and herbicides.

Netherlands Patent No. 121,788, published Sept. 15, 1966, discloses the preparation of compounds of the following Formula and their use as general or selective herbicides:

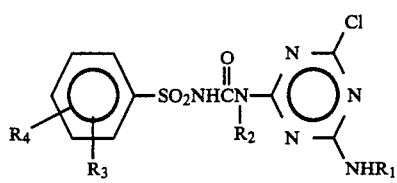

wherein
$R_1$ and $R_2$ may independently be alkyl of 1-4 carbon atoms; and
$R_3$ and $R_4$ may independently be hydrogen, chlorine or alkyl of 1-4 carbon atoms.

U.S. Pat. No. 3,637,366 discloses compounds having the formula:

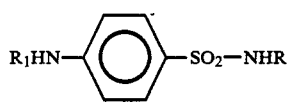

wherein
$R_1$ is hydrogen or lower saturated aliphatic acyl and
$R_2$ is hydrogen, 2-pyrimidinyl, pyridyl, amidino, acetyl or carbamoyl.

The disclosed compounds are said to provide control of crabgrass, cress, endive, clover and *Poa annua*.

French Patent No. 1,468,747 discloses the following para-substituted phenylsulfonamides as being useful as antidiabetic agents:

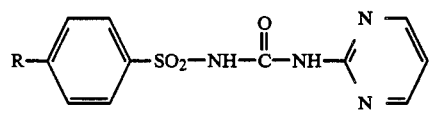

wherein
R=H, halogen, $CF_3$ or alkyl.

Logemann et al., Chem. Ab., 53, 18052g (1959), disclose a number of sulfonamides, including uracil derivatives and those having the formula:

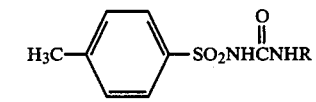

wherein
R is butyl, phenyl or

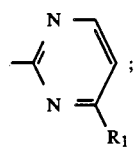

and
$R_1$ is hydrogen or methyl.
When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

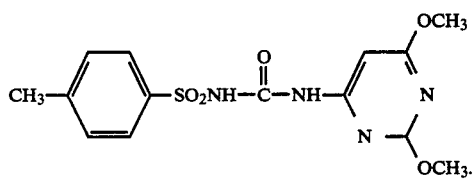

U.S. Pat. No. 4,127,405 teaches compounds which are useful for controlling weeds in wheat having the formula

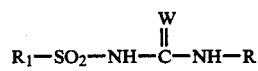

wherein
R is

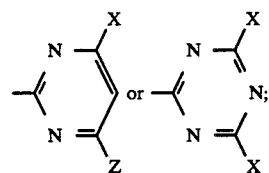

$R_1$ is

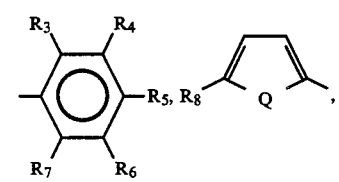

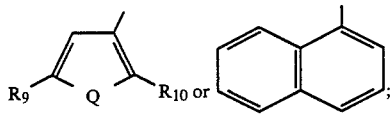

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Z is methyl or methoxy;

or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In EPO Publication No. 0030433, herbicidal sulfonylureas including a derivative of 4-amino heterocycle are taught.

In EPO Publication No. 0035893, published Sept. 16, 1981, the following compounds are taught.

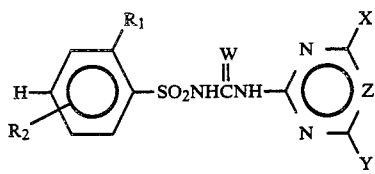

wherein $R_1$ is $R_3S(O)_n$ where $R_3$ is $C_3$–$C_4$ alkyl, $C_3$–$C_4$ alkenyl, cyclopropylmethyl or cyclopentyl;

$R_2$ is H, F, Cl, Br, $CH_3$, $OCH_3$, $CF_3$, $NO_2$, CN or $NH_2$;

n is 0, 1 or 2;

W is O or S;

Z is CH or N;

X is $CH_3$, $C_2H_5$, $CH_3O$, $C_2H_5O$ or $CH_2OCH_3$; and

Y is $CH_3$ or $CH_3O$;

and their agriculturally suitable salts; with the proviso that when $R_2$ is CN, then $R_2$ is not meta to $R_1$; and further provided that when W is S, then n is 0 or 2.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Prevention or minimizing the loss of a portion of such valuable crops by killing, or inhibiting the growth of undesired vegetation is one way of improving this efficiency. A wide variety of materials useful for killing, or inhibiting (controlling) the growth of undesired vegetation is available; such materials are commonly referred to as herbicides. The need still exists however, for more effective herbicides.

SUMMARY OF THE INVENTION

This invention relates to compounds of Formula I, agriculturally suitable compositions containing them, and their method-of-use as general or selective preemergent or post-emergent herbicides or plant growth regulants.

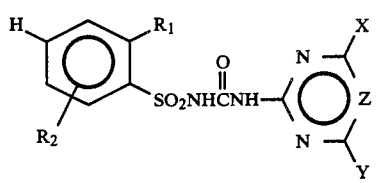

wherein $R_1$ is $S(O)_nR_3$;

$R_2$ is H, F, Cl, Br, $CH_3$, $OCH_3$, $CF_3$ or $NO_2$;

$R_3$ is $C_1$–$C_4$ alkyl, $C_3$–$C_4$ alkenyl or cyclopropylmethyl;

n is 0, 1 or 2;

X is $CH_3$, $C_2H_5$, $CH_3O$, $C_2H_5O$, $CH_2OCH_3$ or Cl;

Y is Cl, F, Br, $NH_2$, $NHCH_3$ or $N(CH_3)_2$; and

Z is CH or N;

and their agriculturally suitable salts; provided that (1) when $R_3$ is $C_3$–$C_4$ alkenyl, then Y is $NH_2$, $NHCH_3$ or $N(CH_3)_2$;

(2) when $R_3$ is $C_1$–$C_2$ alkyl and Y is Cl or Br, then X is other than $CH_3$ or $OCH_3$;

(3) when $R_3$ is $C_1$–$C_3$ alkyl and Y is $NH_2$ or $NHCH_3$, then X is other than Cl, $CH_2CH_3$ or $CH_2OCH_3$;

(4) when Y is Cl, F or Br, then Z is CH and X is $CH_3$, $OCH_3$ or $OCH_2CH_3$; and (5) when X is Cl, then Z is CH and Y is $N(CH_3)_2$.

Preferred for reasons of their higher herbicidal activity, greater plant growth regulant activity and/or more favorble ease of synthesis are:

(1) Compounds of Formula I where n is 2.

(2) Compounds of Preferred 1 where $R_2$ is H, Cl, $CH_3$, $CH_3O$ or $CF_3$.

(3) Compounds of Preferred 2 where X is $CH_3$ or $OCH_3$.

(4) Compounds of Preferred 3 where $R_2$ is H.

Specifically Preferred for reasons of their highest herbicidal activity, greatest plant growth regulant activity and/or most favorable ease of synthesis are:

N-[(4-chloro-6-ethoxypyrimidin-2-yl)aminocarbonyl]-2-(propylsulfonyl)benzenesulfonamide, m.p. 220°–222°;

N-[(4-dimethylamino-6-methoxy-1,3,5-triazin-2-yl)-aminocarbonyl]-2-(methylsulfonyl)benzenesulfonamide, m.p. 192°–195°;

N-[(4-dimethylamino-6-methoxy-1,3,5-triazin-2-yl)-aminocarbonyl]-2-(propylsulfonyl)benzenesulfonamide, m.p. 208°–210°; and N-[(4-chloro-6-methoxypyrimidin-2-yl)aminocarbonyl]-2-(propylsulfonyl)benzenesulfonamide, m.p. 193°–195°.

SYNTHESIS

As shown in Equation 1, the compounds of Formula I can be prepared by reacting an appropriate 2-aminopyrimidine or 2-amino-1,3,5-triazine of Formula III with an appropriately substituted sulfonyl isocyanate of Formula IIa; $R_1$ is $R_3SO_2$ or $R_3S$; $R_2$, $R_3$, X, Y and Z are as previously defined.

EQUATION 1

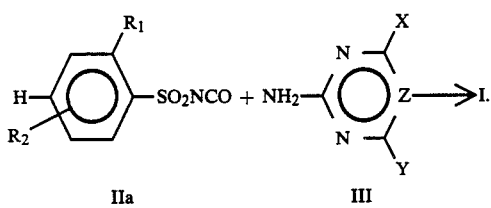

The reaction is best carried out in an inert aprotic organic solvent such as methylene chloride, tetrahydrofuran or acetonitrile, at ambient pressure and temperature. The mode of addition is not critical; however, it is often convenient to add the sulfonyl isocyanate to a stirred suspension of amine III. Since such isocyanates are usually liquid, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether and filtration.

The intermediate sulfonyl isocyanates of Formula IIa can be prepared by reacting corresponding sulfonamides with phosgene in the presence of n-butyl isocyanate at reflux in a solvent such as xylene, according to the procedure of H. Ulrich and A. A. Y. Sayigh, *Newer Methods of Preparative Organic Chemistry*, Vol. VI, p. 223–241, Academic Press, New York and London, W. Foerst Ed. In cases where formation of the desired sulfonyl isocyanate is difficult by the above procedure, the sulfonylurea formed by the reaction of butyl isocyanate with the appropriate sulfonamide is treated with phosgene according to the above reference.

These intermediates are prepared from the parent sulfonamides of Formula IIb as shown in Equation 2 by the reaction of the n-butylsulfonylurea with phosgene as described above. In Equation 2, $R_1$ is $R_3SO_2$ or $R_3S$ and $R_2$ and $R_3$ are as previously defined.

EQUATION 2

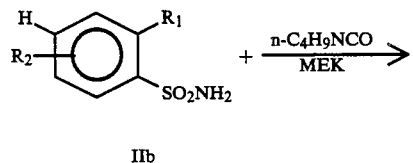

-continued

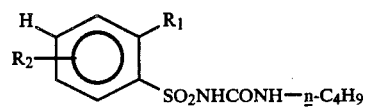

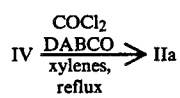

A mixture of the appropriate sulfonylurea, IV and a catalytic amount of 1,4-diaza[2.2.2]bicyclooctane (DABCO) in xylene, chlorobenzene or other inert solvent of sufficiently high boiling point (e.g. 135° C.) is heated to approximately 135° C. Phosgene is added to the mixture until an excess of phosgene is present as indicated by a drop in the boiling point. The mixture is heated further to drive off the excess phosgene, cooled and filtered to remove a small amount of insoluble by-products. The solvent and alkylisocyanate are removed in vacuo leaving a residue which is the crude sulfonylisocyanate IIa.

The sulfonylisocyanates of Formula IIa may also be prepared by reacting sulfonamides of Formula IIb with thionyl chloride and then phosgene as taught in EPO Publication No. 35893.

Certain compounds of Formula I are best prepared by heating a mixture of the arylsulfonylphenylcarbamate of Formula IIc and an appropriate 2-aminopyrimidine or 2-amino-1,3,5-triazine of Formula III in a solvent of sufficiently high boiling point, for example dioxane, as shown in Equation 3. The carbamates of Formula IIc are readily prepared from the corresponding sulfonamides of Formula IIb, where $R_1$ and $R_2$ are as previously defined, and diphenylcarbamate in the presence of base.

EQUATION 3

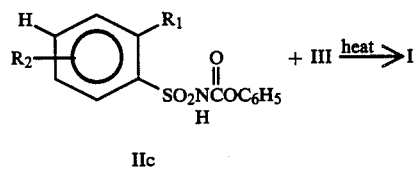

The compounds of Formula I can also be prepared from the sulfonamides of Formula IIb and the appropriate heterocyclic carbamate of Formula IIIa as shown in Equation 4. Contacting IIb with trimethylaluminum is followed by addition of IIIa. Heating the resulting mixture in dichloromethane will give I after acidic workup. The heterocyclic carbamates of Formula IIIa can be readily prepared from the corresponding amines III by standard literature procedures.

EQUATION 4

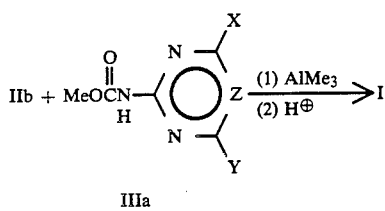

IIIa

The sulfonamides of Formula IIb can be prepared by a variety of procedures reported in the literature. As shown in Equation 5, the thioether of Formula VI may be prepared from the appropriate 2-aminothiophenol V and an alkyl halide as described in the literature, e.g., R. N. Prasad et al., *Can. J. Chem.*, 44, 1247 (1966). The formation of the benzenesulfonyl chloride and the corresponding sulfonamide IId has been previously described (co-pending application Ser. No. 192,034, filed Sept. 29, 1980). The oxidation of IId to the corresponding 2-alkylsulfinyl- or 2-alkylsulfonylbenzenesulfonamides of Formulae IIe and IIf may be carried out utilizing a variety of standard literature procedures, including m-chloroperbenzoic acid (C. R. Johnson, et al., *Tetradedron* 25, 5649 (1969)), or with aqueous hydrogen peroxide in acetic acid (F. G. Bordwell, et al., *J. Amer. Chem. Soc.*, 77, 1141 (1955)).

EQUATION 5

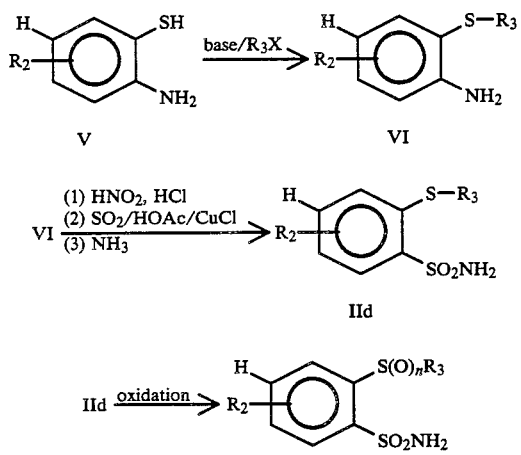

IIe n = 1
IIf n = 2

Compounds of Formula IIb wherein n≠1 may also be prepared from 2-halonitrobenzenes of Formula VII where A is a halogen as outlined in Equation 6. Halide displacement in VII by thiols (n=0) or sulfinates (n=2) is widely reported in the literature (for general reviews see, "Organic Chemistry of Sulfur", S. Oae, ed., Plenum Press, New York, 1977, pp. 232–233; Reid, "Organic Chemistry of Bivalent Sulfur," Chemical Publishing Co., New York, Vol. 2, pp. 16–21, 24–29; Vol. 3, pp. 11–14; Peach, in Patai, "The Chemistry of the Thiol Group," pt. 2, pp. 735–744, John Wiley and Sons, Inc., New York, 1974).

EQUATION 6

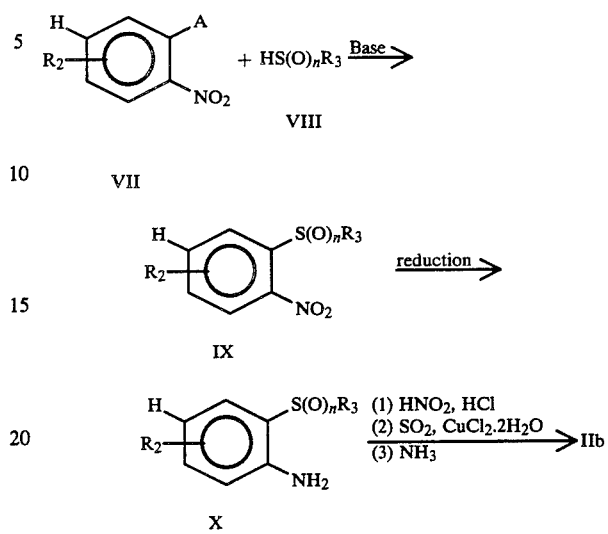

Compounds of Formula IX (n=0 or 2) may also be prepared as shown in Equation 7 (in addition to references cited above, see *Zn Obshch. Khim*, 35 (8) 1361 (1965) and *J. Chem. Soc.*, 763 (1946)). Reduction of IX to the amine X can be carried out by a variety of standard literature procedures, including catalytic hydrogenation (Rylander, "Catalytic Hydrogenation over Platinum Metals," pp. 168–202, Academic Press, Inc., New York, 1967) and reduction with iron (D. Cowsley et al., *Synthesis* 118 (1977)) or stannous chloride (*Org. Synth.*, Coll. Vol. 2, 130 (1943); ibid, 3, 240, 453 (1955)) in acidic medium. Conversion of X to IIb has been discussed previously (Equation 5).

EQUATION 7

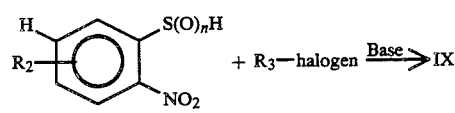

In some cases it is best to oxidize the thioethers of Formula IXa to the corresponding sulfones IXb prior to reduction and subsequent diazotization, as shown in Equation 8.

EQUATION 8

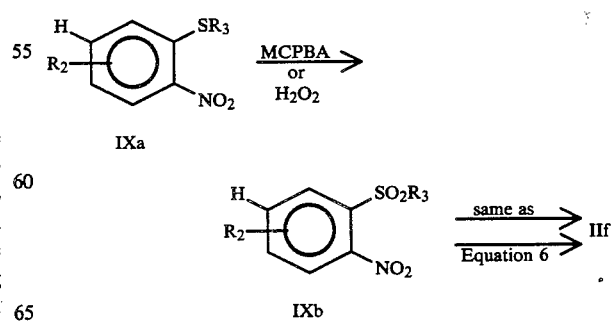

Ortho-lithiation of appropriately substituted benzene derivatives also provides a route to sulfonamides of Formula IIb. As shown in Equation 9, the t-butylbenzenesulfonamides of Formula XI may be ortholithiated [for general review, see H. W. Gschwend et al., *Organic Reactions*, 26, 1 (1979)] and then trapped with sulfur, followed by alkyl halide, or trapped with a disulfide to give sulfonamides of Formula IId [S. Gronowitz et al., *Acta. Chem. Scand.*, 21, 812 (1967) and *Chem. Ber.*, 99, 3215 (1966)]. Reactions of XII with sulfur dioxide, followed by alkyl halide ($R_3$-hal.) will give sulfonamides of Formula IIf [*JACS*, 74, 5177 (1952)].

EQUATION 9

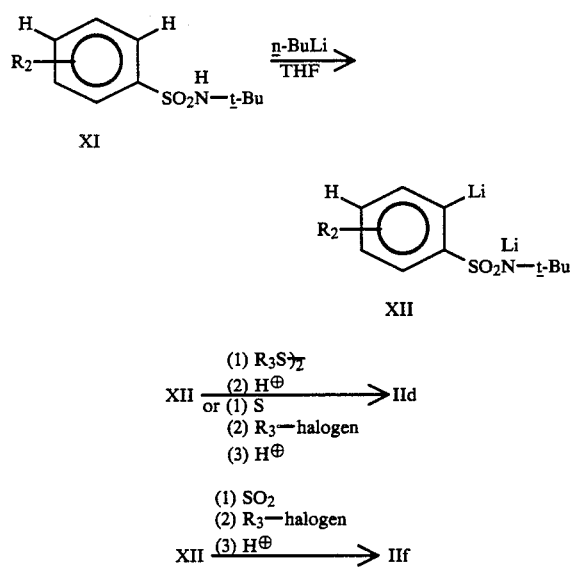

The lithium sulfonates of Formula XIII can also be ortho-lithiated to give compounds of Formula XIV as shown in Equation 10. Treatment of XIV with sulfur electrophiles as in Equation 9 will give the sulfonates of Formula XV (for example, see J. C. Martin et al., *JOC*, 45, 3728 (1980)]. Conversion of XV to the sulfonamides of Formula IIb can be accomplished using thionyl chloride and a catalytic amount of dimethylformamide and then treating the sulfonyl chloride with ammonia.

EQUATION 10

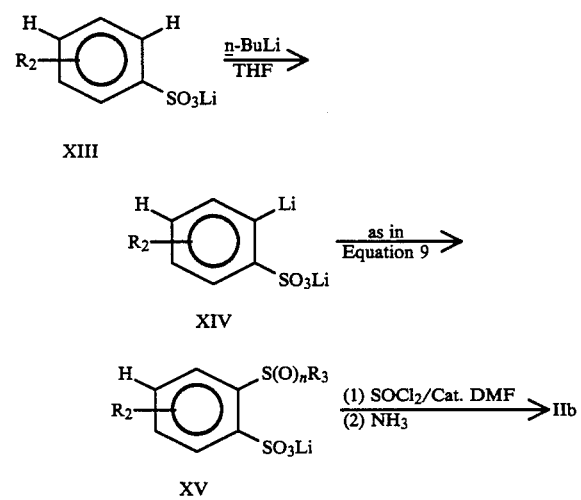

Sulfonamides of Formula IId can also be prepared by reaction of the chlorosulfonamides of Formula IIg and the appropriate mercaptan of Formula XVI in a high boiling solvent, for example, dimethylformamide, as shown in Equation 11. The preparation of the sulfonamides IIg is described in U.S. Pat. No. 4,169,719 and U.S. Pat. No. 4,127,405, which are herein incorporated by reference.

EQUATION 11

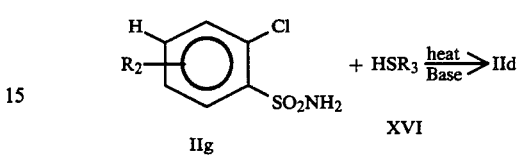

Compounds of Formula I may also be prepared by the reaction of the substituted sulfonamides of Formula IIb with an appropriate heterocyclic isocyanate as previously described (co-pending applications Ser. No. 098,725 and Ser. No. 098,722).

Compounds of Formula Ib, where $R_1$ is equal to $SOR_3$ can be prepared from the appropriate compounds of Formula Ia where $R_1$ is equal to $SR_3$; $R_2$, X, Y and Z being as previously defined, by oxidation with m-chloroperbenzoic acid according to Equation 12.

EQUATION 12

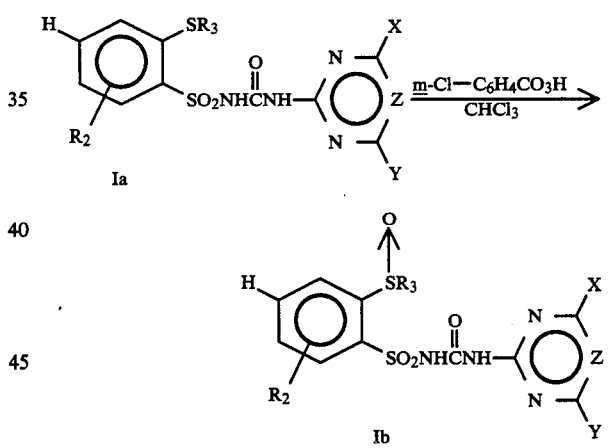

The reaction can be carried out by mixing equivalent amounts of Ia with m-chloroperbenzoic acid in an inert solvent such as chloroform and stirring at 0° C. to reflux for 12-24 hours after which the insoluble m-chlorobenzoic acid produced is removed by filtration and the chloroform solution containing the desired sulfoxide is concentrated to yield the crude product. The product can be purified further by dissolving it in aqueous base of pH 10 and adjusting the pH to 4 to precipitate the desired compound while leaving the m-chlorobenzoic acid in solution as its sodium salt. Treatment of Ia with one equivalent of hydrogen peroxide in glacial acetic acid at 0° C. to room temperature will also give sulfoxide Ib.

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines", Vol. XVI of the above series. 2-Amino-1,3,5-triazines can be synthesized according to the methods described by E. M. Smolin and L. Rapaport in "s-Triazines and Derivatives," Vol. XIII of the same series.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and parts are by weight unless otherwise designated.

EXAMPLE 1

N-[(4-Chloro-6-ethoxypyrimidin-2-yl)aminocarbonyl]-2-(propylsulfonyl)benzenesulfonamide To a suspension of 2-propylsulfonylbenzenesulfonyl isocyanate (1.67 g, 5.76 mmol) in dry acetonitrile was added 2-amino-4-chloro-6-ethoxypyrimidine (1.00 g, 5.76 mmol). After stirring at room temperature overnight, the reaction mixture was filtered and the solid washed with 1-chlorobutane to give the product as a white powder melting at 220°-222° C.

EXAMPLE 2

N-[(4-Chloro-6-methoxypyrimidin-2-yl)aminocarbonyl]-2-(propylsulfonyl)benzenesulfonamide To a suspension of 2-propylsulfonylbenzenesulfonyl isocyanate (1.74 g, 6.00 mmol) in dry acetonitrile (25 ml) was added 2-amino-4-chloro-6-ethoxypyrimidine (1.00 g, 6.00 mmol). After stirring at room temperature overnight, the reaction mixture was filtered to yield the product as a white powder melting at 193°-195° C.

EXAMPLE 3

N-[(4-Dimethylamino-6-methoxy-1,3,5-triazin-2-yl)-aminocarbonyl]-2-(methylsulfonyl)benzenesulfonamide To a suspension of 2-amino-4-dimethylamino-6-methoxy-1,3,5-triazine (1.02 g, 6.00 mmol) in dry acetonitrile (30 ml) was added 2-methylsulfonylbenzenesulfonyl isocyanate (1.50 g, 6.00 mmol). After stirring at room temperature overnight, the reaction mixture was filtered and the solid washed with acetonitrile to give the product as a white powder with a melting point of 192°-195° C.

Using procedures similar to those given in Examples 1-3 and Equations 1-12, the following compounds may be prepared.

TABLE I

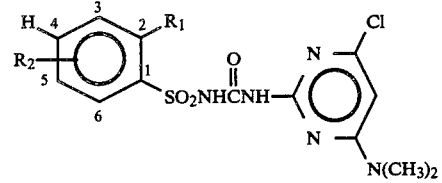

| $R_1$ | $R_2$ | m.p. (°C.) |
|---|---|---|
| $SCH_3$ | H | |
| $SOCH_3$ | H | |
| $SO_2CH_3$ | H | 231–235° |
| $SC_2H_5$ | H | |
| $SOC_2H_5$ | H | |
| $SO_2C_2H_5$ | H | 151–155° |
| $S(CH_2)_2CH_3$ | H | |
| $SO(CH_2)_2CH_3$ | H | |
| $SO_2(CH_2)_2CH_3$ | H | |
| $SCH(CH_3)_2$ | H | |
| $SOCH(CH_3)_2$ | H | |
| $SO_2CH(CH_3)_2$ | H | |
| $S(CH_2)_3CH_3$ | H | |
| $SO(CH_2)_3CH_3$ | H | |
| $SO_2(CH_2)_3CH_3$ | H | |
| $SCH_2CH(CH_3)_2$ | H | |
| $SOCH_2CH(CH_3)_2$ | H | |
| $SO_2CH_2CH(CH_3)_2$ | H | |
| $SCH(CH_3)CH_2CH_3$ | H | |
| $SOCH(CH_3)CH_2CH_3$ | H | |
| $SO_2CH(CH_3)CH_2CH_3$ | H | |
| $SC(CH_3)_3$ | H | |
| $SOC(CH_3)_3$ | H | |
| $SO_2C(CH_3)_3$ | H | |
| $SCH_2CH=CH_2$ | H | |
| $SOCH_2CH=CH_2$ | H | |
| $SO_2CH_2CH=CH_2$ | H | |
| $SCH=CHCH_3$ | H | |
| $SOCH=CHCH_3$ | H | |
| $SO_2CH=CHCH_3$ | H | |
| $SCH_2CH=CHCH_3$ | H | |
| $SOCH_2CH=CHCH_3$ | H | |
| $SO_2CH_2CH=CHCH_3$ | H | |
| $SCH_2C(CH_3)=CH_2$ | H | |
| $SOCH_2C(CH_3)=CH_2$ | H | |
| $SO_2CH_2C(CH_3)=CH_2$ | H | |
| $SCH_2CH{<}^{CH_2}_{CH_2}$ | H | |
| $SOCH_2CH{<}^{CH_2}_{CH_2}$ | H | |
| $SO_2CH_2CH{<}^{CH_2}_{CH_2}$ | H | |
| $SO_2CH_3$ | 3-Cl | |
| $SO_2CH_3$ | 3-$CH_3$ | |
| $SO_2CH_3$ | 3-$CF_3$ | |
| $SO_2CH_3$ | 5-F | |
| $SO_2CH_3$ | 5-Cl | |
| $SO_2CH_3$ | 5-Br | |
| $SO_2CH_3$ | 5-$CH_3$ | |
| $SO_2CH_3$ | 5-$OCH_3$ | |
| $SO_2CH_3$ | 5-$CF_3$ | |
| $SO_2CH_3$ | 5-$NO_2$ | |
| $SO_2CH_3$ | 6-Cl | |

TABLE I-continued

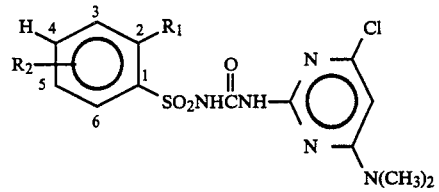

| R₁ | R₂ | m.p. (°C.) |
|---|---|---|
| SO$_2$CH$_3$ | 6-CH$_3$ | |
| SO$_2$CH$_3$ | 6-OCH$_3$ | |
| SO$_2$C$_2$H$_5$ | 3-CH$_3$ | |
| SO$_2$C$_2$H$_5$ | 3-Cl | |
| SO$_2$C$_2$H$_5$ | 3-CF$_3$ | |
| SO$_2$C$_2$H$_5$ | 3-Cl | |
| SO$_2$C$_2$H$_5$ | 5-Br | |
| SO$_2$C$_2$H$_5$ | 5-CH$_3$ | |
| SO$_2$C$_2$H$_5$ | 5-CF$_3$ | |
| SO$_2$C$_2$H$_5$ | 5-OCH$_3$ | |
| SO$_2$C$_2$H$_5$ | 6-CH$_3$ | |
| SO$_2$(CH$_2$)$_2$CH$_3$ | 3-Br | |
| SO$_2$(CH$_2$)$_2$CH$_3$ | 3-Cl | |
| SO$_2$(CH$_2$)$_2$CH$_3$ | 5-Cl | |
| SO$_2$(CH$_2$)$_2$CH$_3$ | 5-CH$_3$ | |
| SO$_2$(CH$_2$)$_2$CH$_3$ | 5-Br | |
| SO$_2$(CH$_2$)$_2$CH$_3$ | 5-CF$_3$ | |
| SO$_2$(CH$_2$)$_2$CH$_3$ | 5-OCH$_3$ | |
| SO$_2$(CH$_2$)$_2$CH$_3$ | 6-CH$_3$ | |
| SO$_2$(CH$_2$)$_2$CH$_3$ | 6-Cl | |
| SO$_2$CH(CH$_3$)$_2$ | 5-CF$_3$ | |
| S(CH$_2$)$_3$CH$_3$ | 3-CH$_3$ | |
| SOCH$_2$CH(CH$_3$)$_2$ | 5-CH$_3$ | |
| SO$_2$CH(CH$_3$)CH$_2$CH$_3$ | 5-Br | |
| SO$_2$C(CH$_3$)$_3$ | 5-CF$_3$ | |
| SO$_2$CH$_2$CH=CH$_2$ | 3-CH$_3$ | |
| SO$_2$CH$_2$CH=CH$_2$ | 5-CF$_3$ | |
| SO$_2$CH$_2$CH=CH$_2$ | 5-Br | |
| SO$_2$CH$_2$CH=CH$_2$ | 5-CH$_3$ | |
| SO$_2$CH$_2$CH=CH$_2$ | 6-NO$_2$ | |
| SO$_2$CH$_2$CH=CH$_2$ | 6-OCH$_3$ | |
| SO$_2$CH$_2$CH=CHCH$_3$ | 5-CF$_3$ | |
| SCH$_2$CH(cyclopropyl) | 3-CH$_3$ | |
| SCH$_2$CH(cyclopropyl) | 5-Br | |
| SCH$_2$CH(cyclopropyl) | 5-NO$_2$ | |
| SCH$_2$CH(cyclopropyl) | 6-F | |

TABLE II

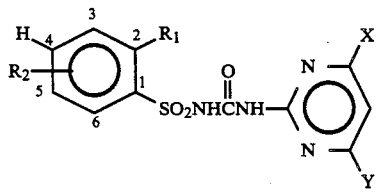

| R₁ | R₂ | X | Y | m.p. (°C.) |
|---|---|---|---|---|
| S(CH$_2$)$_2$CH$_3$ | H | CH$_3$ | Cl | |
| SO(CH$_2$)$_2$CH$_3$ | H | CH$_3$ | Cl | |
| SO$_2$(CH$_2$)$_2$CH$_3$ | H | CH$_3$ | Cl | |
| SCH(CH$_3$)$_2$ | H | CH$_3$ | Cl | |

TABLE II-continued

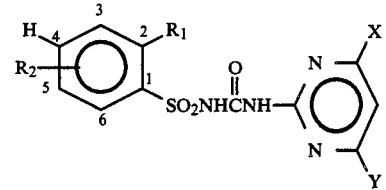

| R₁ | R₂ | X | Y | m.p. (°C.) |
|---|---|---|---|---|
| SOCH(CH$_3$)$_2$ | H | CH$_3$ | Cl | |
| SO$_2$CH(CH$_3$)$_2$ | H | CH$_3$ | Cl | |
| S(CH$_2$)$_3$CH$_3$ | H | CH$_3$ | Cl | |
| SO(CH$_2$)$_3$CH$_3$ | H | CH$_3$ | Cl | |
| SO$_2$(CH$_2$)$_3$CH$_3$ | H | CH$_3$ | Cl | |
| SCH$_2$CH(CH$_3$)$_2$ | H | CH$_3$ | Cl | |
| SOCH$_2$CH(CH$_3$)$_2$ | H | CH$_3$ | Cl | |
| SO$_2$CH$_2$CH(CH$_3$)$_2$ | H | CH$_3$ | Cl | |
| SCH(CH$_3$)CH$_2$CH$_3$ | H | CH$_3$ | Cl | |
| SOCH(CH$_3$CH$_2$CH$_3$ | H | CH$_3$ | Cl | |
| SO$_2$CH(CH$_3$)CH$_2$CH$_3$ | H | CH$_3$ | Cl | |
| SC(CH$_3$)$_3$ | H | CH$_3$ | Cl | |
| SOC(CH$_3$)$_3$ | H | CH$_3$ | Cl | |
| SO$_2$C(CH$_3$)$_3$ | H | CH$_3$ | Cl | |
| SCH$_2$CH(cyclopropyl) | H | CH$_3$ | Cl | |
| SOCH$_2$CH(cyclopropyl) | H | CH$_3$ | Cl | |
| SO$_2$CH$_2$CH(cyclopropyl) | H | CH$_3$ | Cl | |
| S(CH$_2$)$_2$CH$_3$ | H | OCH$_3$ | Cl | 160–162° |
| SO(CH$_2$)$_2$CH$_3$ | H | OCH$_3$ | Cl | |
| SO$_2$(CH$_2$)$_2$CH$_3$ | H | OCH$_3$ | Cl | 193–195° |
| SCH(CH$_3$)$_2$ | H | OCH$_3$ | Cl | |
| SOCH(CH$_3$)$_2$ | H | OCH$_3$ | Cl | |
| SO$_2$CH(CH$_3$)$_2$ | H | OCH$_3$ | Cl | |
| S(CH$_2$)$_3$CH$_3$ | H | OCH$_3$ | Cl | |
| SO(CH$_2$)$_3$CH$_3$ | H | OCH$_3$ | Cl | |
| SO$_2$(CH$_2$)$_3$CH$_3$ | H | OCH$_3$ | Cl | |
| SCH$_2$CH(CH$_3$)$_2$ | H | OCH$_3$ | Cl | |
| SOCH$_2$CH(CH$_3$)$_2$ | H | OCH$_3$ | Cl | |
| SO$_2$CH$_2$CH(CH$_3$)$_2$ | H | OCH$_3$ | Cl | |
| SCH(CH$_3$)CH$_2$CH$_3$ | H | OCH$_3$ | Cl | |
| SOCH(CH$_3$)CH$_2$CH$_3$ | H | OCH$_3$ | Cl | |
| SO$_2$CH(CH$_3$)CH$_2$CH$_3$ | H | OCH$_3$ | Cl | |
| SC(CH$_3$)$_3$ | H | OCH$_3$ | Cl | |
| SOC(CH$_3$)$_3$ | H | OCH$_3$ | Cl | |
| SO$_2$C(CH$_3$)$_3$ | H | OCH$_3$ | Cl | |
| SCH$_2$CH(cyclopropyl) | H | OCH$_3$ | Cl | |
| SOCH$_2$CH(cyclopropyl) | H | OCH$_3$ | Cl | |
| SO$_2$CH$_2$CH(cyclopropyl) | H | OCH$_3$ | Cl | |
| S(CH$_2$)$_2$CH$_3$ | H | OC$_2$H$_5$ | Cl | |
| SO(CH$_2$)$_2$CH$_3$ | H | OC$_2$H$_5$ | Cl | |
| SO$_2$(CH$_2$)$_2$CH$_3$ | H | OC$_2$H$_5$ | Cl | 220–222° |
| SCH(CH$_3$)$_2$ | H | OC$_2$H$_5$ | Cl | |
| SOCH(CH$_3$)$_2$ | H | OC$_2$H$_5$ | Cl | |
| SO$_2$CH(CH$_3$)$_2$ | H | OC$_2$H$_5$ | Cl | |
| S(CH$_2$)$_3$CH$_3$ | H | OC$_2$H$_5$ | Cl | |

TABLE II-continued

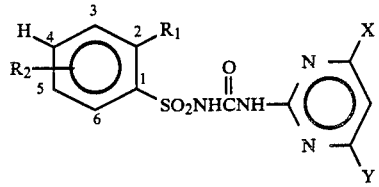

| R₁ | R₂ | X | Y | m.p. (°C.) |
|---|---|---|---|---|
| SO(CH₂)₃CH₃ | H | OC₂H₅ | Cl | |
| SO₂(CH₂)₃CH₃ | H | OC₂H₅ | Cl | |
| SCH₂CH(CH₃)₂ | H | OC₂H₅ | Cl | |
| SOCH₂CH(CH₃)₂ | H | OC₂H₅ | Cl | |
| SO₂CH₂CH(CH₃)₂ | H | OC₂H₅ | Cl | |
| SCH(CH₃)CH₂CH₃ | H | OC₂H₅ | Cl | |
| SOCH(CH₃)CH₂CH₃ | H | OC₂H₅ | Cl | |
| SO₂CH(CH₃)CH₂CH₃ | H | OC₂H₅ | Cl | |
| SC(CH₃)₃ | H | OC₂H₅ | Cl | |
| SOC(CH₃)₃ | H | OC₂H₅ | Cl | |
| SO₂C(CH₃)₃ | H | OC₂H₅ | Cl | |
| SCH₂—CH(CH₂CH₂) (cyclopropyl) | H | OC₂H₅ | Cl | |
| SOCH₂—CH(CH₂CH₂) (cyclopropyl) | H | OC₂H₅ | Cl | |
| SO₂CH₂—CH(CH₂CH₂) (cyclopropyl) | H | OC₂H₅ | Cl | |
| SO₂(CH₂)₂CH₃ | H | CH₃ | F | |
| SO₂(CH₂)₂CH₃ | H | CH₃ | Br | |
| SO₂(CH₂)₂CH₃ | 3-Cl | CH₃ | Cl | |
| SO₂(CH₂)₂CH₃ | 3-OCH₃ | CH₃ | Cl | |
| SO₂(CH₂)₂CH₃ | 3-CF₃ | CH₃ | Cl | |
| SO₂(CH₂)₂CH₃ | 5-F | CH₃ | Cl | |
| SO₂(CH₂)₂CH₃ | 5-Cl | CH₃ | Cl | |
| SO₂(CH₂)₂CH₃ | 5-Br | CH₃ | Cl | |
| SO₂(CH₂)₂CH₃ | 5-CH₃ | CH₃ | Cl | |
| SO₂(CH₂)₂CH₃ | 5-OCH₃ | CH₃ | Cl | |
| SO₂(CH₂)₂CH₃ | 5-CF₃ | CH₃ | Cl | |
| SO₂(CH₂)₂CH₃ | 5-NO₂ | CH₃ | Cl | |
| SO₂(CH₂)₂CH₃ | 6-Cl | CH₃ | Cl | |
| SO₂(CH₂)₂CH₃ | 6-CH₃ | CH₃ | Cl | |
| SO₂(CH₂)₂CH₃ | 6-OCH₃ | CH₃ | Cl | |
| SO₂CH(CH₃)₂ | 5-CH₃ | CH₃ | Cl | |
| SO₂CH(CH₃)₂ | 5-CF₃ | CH₃ | Cl | |
| SO₂CH(CH₃)₂ | 5-Cl | CH₃ | Cl | |
| SO₂(CH₂)₃CH₃ | 3-CH₃ | CH₃ | Cl | |
| SO₂(CH₂)₃CH₃ | 5-Cl | CH₃ | Cl | |
| SO₂(CH₂)₃CH₃ | 5-OCH₃ | CH₃ | Cl | |
| SCH(CH₃)CH₂CH₃ | H | CH₃ | F | |
| SOCH₂CH(CH₃)₂ | H | CH₃ | Br | |
| SO₂C(CH₃)₃ | 5-Br | CH₃ | Cl | |
| SO₂CH₂CH(CH₂CH₂) (cyclopropyl) | H | CH₃ | F | |
| SO₂CH₂CH(CH₂CH₂) (cyclopropyl) | H | CH₃ | Br | |
| SO₂CH₂CH(CH₂CH₂) (cyclopropyl) | 6-Br | CH₃ | Cl | |
| SO₂CH₂CH(CH₂CH₃) | 5-CF₃ | CH₃ | Cl | |
| SO₂(CH₂)₂CH₃ | H | OCH₃ | F | |
| SO₂(CH₂)₂CH₃ | H | OCH₃ | Br | |
| SO₂(CH₂)₂CH₃ | 5-CH₃ | OCH₃ | Cl | |
| SO₂(CH₂)₂CH₃ | 5-Br | OCH₃ | Cl | |
| SO₂(CH₂)₂CH₃ | 5-OCH₃ | OCH₃ | Cl | |
| SO₂(CH₂)₂CH₃ | 5-CF₃ | OCH₃ | Cl | |
| SO₂(CH₂)₂CH₃ | 6-CH₃ | OCH₃ | Cl | |
| SO₂(CH₂)₂CH₃ | 6-Cl | OCH₃ | Cl | |
| SO₂(CH₂)₃CH₃ | 3-F | OCH₃ | Cl | |
| SO₂(CH₂)₃CH₃ | 3-NO₂ | OCH₃ | Cl | |
| SO₂(CH₂)₃CH₃ | 5-CH₃ | OCH₃ | Cl | |
| SO₂(CH₂)₃CH₃ | 5-OCF₃ | OCH₃ | Cl | |
| SO₂CH(CH₃)CH₂CH₃ | H | OCH₃ | F | |
| SO₂CH(CH₃)CH₂CH₃ | H | OCH₃ | Br | |
| SO₂CH(CH₃)CH₂CH₃ | 5-Cl | OCH₃ | Cl | |
| SO₂CH(CH₃)CH₂CH₃ | 5-OCH₃ | OCH₃ | Cl | |
| SO₂CH(CH₃)CH₂CH₃ | 5-CF₃ | OCH₃ | Cl | |
| SO₂CH(CH₃)CH₂CH₃ | 5-NO₂ | OCH₃ | Cl | |
| SO₂CH₂CH(CH₂CH₂) (cyclopropyl) | H | OCH₃ | F | |
| SO₂CH₂CH(CH₂CH₂) (cyclopropyl) | H | OCH₃ | Br | |
| SO₂CH₂CH(CH₂CH₂) (cyclopropyl) | 6-Cl | OCH₃ | Cl | |
| S(CH₂)₂CH₃ | H | OCH₃ | F | |
| S(CH₂)₂CH₃ | H | OCH₃ | Br | |
| S(CH₂)₂CH₃ | 5-CF₃ | OCH₃ | Cl | |
| S(CH₂)₂CH₃ | 6-Cl | OCH₃ | Cl | |
| SO₂(CH₂)₂CH₃ | H | OC₂H₅ | F | |
| SO₂(CH₂)₂CH₃ | H | OC₂H₅ | Br | |
| SO₂(CH₂)₂CH₃ | 3-CF₃ | OC₂H₅ | Cl | |
| SO₂(CH₂)₂CH₃ | 5-Cl | OC₂H₅ | Cl | |
| SO₂(CH₂)₂CH₃ | 4-OCH₃ | OC₂H₅ | Cl | |
| SO₂(CH₂)₂CH₃ | 5-NO₂ | OC₂H₅ | Cl | |
| SO₂(CH₂)₂CH₃ | 5-CH₃ | OC₂H₅ | Cl | |
| SO₂(CH₂)₂CH₃ | 6-CH₃ | OC₂H₅ | Cl | |
| SO₂(CH₂)₂CH₃ | 6-Cl | OC₂H₅ | Cl | |
| SOCH(CH₃)₂ | 3-CH₃ | OC₂H₅ | Cl | |
| SOCH(CH₃)₂ | 5-Cl | OC₂H₅ | Cl | |
| SOCH(CH₃)₂ | 6-Br | OC₂H₅ | Cl | |
| SCH₂CH(CH₃)₂ | 3-CF₃ | OC₂H₅ | Cl | |
| SCH₂CH(CH₃)₂ | 5-OCH₃ | OC₂H₅ | Cl | |
| SCH₂CH(CH₃)₂ | 6-NO₂ | OC₂H₅ | Cl | |
| SO₂C(CH₃)₃ | H | OC₂H₅ | F | |
| SO₂C(CH₃)₃ | H | OC₂H₅ | Br | |
| SO₂C(CH₃)₃ | 5-Br | OC₂H₅ | Cl | |
| SO₂C(CH₃)₃ | 5-CH₃ | OC₂H₅ | Cl | |
| SO₂C(CH₃)₃ | 6-CF₃ | OC₂H₅ | Cl | |
| SCH₂CH(CH₂CH₂) (cyclopropyl) | 3-Br | OC₂H₅ | Cl | |
| SCH₂CH(CH₂CH₂) (cyclopropyl) | 5-CF₃ | OC₂H₅ | Cl | |

TABLE II-continued

Structure: phenyl ring with positions labeled (H at 4, R₁ at 2, R₂ at 5, position 1 bears SO₂NHC(O)NH-pyrimidine with X and Y substituents)

| R₁ | R₂ | X | Y | m.p. (°C) |
|---|---|---|---|---|
| SCH₂CH(CH₂CH₂) [cyclopropyl] | 6-CH₃ | OC₂H₅ | Cl | |
| SO₂CH₃ | H | OC₂H₅ | Cl | 188–190° |

TABLE III

Structure: phenylsulfonylurea linked to pyrimidine with X and N(CH₃)₂ substituents

| R₁ | R₂ | X | m.p. (°C) |
|---|---|---|---|
| SCH₃ | H | CH₃ | |
| SOCH₃ | H | CH₃ | |
| SO₂CH₃ | H | CH₃ | 239–242° |
| SC₂H₅ | H | CH₃ | |
| SOC₂H₅ | H | CH₃ | |
| SO₂C₂H₅ | H | CH₃ | |
| S(CH₂)₂CH₃ | H | CH₃ | |
| SO(CH₂)₂CH₃ | H | CH₃ | |
| SO₂(CH₂)₂CH₃ | H | CH₃ | |
| SCH(CH₃)₂ | H | CH₃ | |
| SOCH(CH₃)₂ | H | CH₃ | |
| SO₂CH(CH₃)₂ | H | CH₃ | |
| S(CH₂)₃CH₃ | H | CH₃ | |
| SO(CH₂)₃CH₃ | H | CH₃ | |
| SO₂(CH₂)₃CH₃ | H | CH₃ | |
| SCH₂CH(CH₃)₂ | H | CH₃ | |
| SOCH₂CH(CH₃)₂ | H | CH₃ | |
| SO₂CH₂CH(CH₃)₂ | H | CH₃ | |
| SCH(CH₃)CH₂CH₃ | H | CH₃ | |
| SOCH(CH₃)CH₂CH₃ | H | CH₃ | |
| SO₂CH(CH₃)CH₂CH₃ | H | CH₃ | |
| SC(CH₃)₃ | H | CH₃ | |
| SOC(CH₃)₃ | H | CH₃ | |
| SO₂C(CH₃)₃ | H | CH₃ | |
| SCH₂CH=CH₂ | H | CH₃ | |
| SOCH₂CH=CH₂ | H | CH₃ | |
| SO₂CH₂CH=CH₂ | H | CH₃ | |
| SCH₂CH=CHCH₃ | H | CH₃ | |
| SOCH₂CH=CHCH₃ | H | CH₃ | |
| SO₂CH₂CH=CHCH₃ | H | CH₃ | |
| SCH₂CH(cyclopropyl) | H | CH₃ | |
| SOCH₂CH(cyclopropyl) | H | CH₃ | |
| SO₂CH₂CH(cyclopropyl) | H | CH₃ | |
| SCH₃ | H | OCH₃ | |
| SOCH₃ | H | OCH₃ | |
| SO₂CH₃ | H | OCH₃ | 208–210° |
| SC₂H₅ | H | OCH₃ | |

TABLE III-continued

| R₁ | R₂ | X | m.p. (°C) |
|---|---|---|---|
| SOC₂H₅ | H | OCH₃ | |
| SO₂C₂H₅ | H | OCH₃ | 189–190° |
| S(CH₂)₂CH₃ | H | OCH₃ | |
| SO(CH₂)₂CH₃ | H | OCH₃ | |
| SO₂(CH₂)₂CH₃ | H | OCH₃ | |
| SCH(CH₃)₂ | H | OCH₃ | |
| SOCH(CH₃)₂ | H | OCH₃ | |
| SO₂CH(CH₃)₂ | H | OCH₃ | |
| S(CH₂)₃CH₃ | H | OCH₃ | |
| SO(CH₂)₃CH₃ | H | OCH₃ | |
| SO₂(CH₂)₃CH₃ | H | OCH₃ | |
| SCH₂CH(CH₃)₂ | H | OCH₃ | |
| SOCH₂CH(CH₃)₂ | H | OCH₃ | |
| SO₂CH₂CH(CH₃)₂ | H | OCH₃ | |
| SCH(CH₃)CH₂CH₃ | H | OCH₃ | |
| SOCH(CH₃)CH₂CH₃ | H | OCH₃ | |
| SO₂CH(CH₃)CH₂CH₃ | H | OCH₃ | |
| SC(CH₃)₃ | H | OCH₃ | |
| SOC(CH₃)₃ | H | OCH₃ | |
| SO₂C(CH₃)₃ | H | OCH₃ | |
| SCH₂CH=CH₂ | H | OCH₃ | |
| SOCH₂CH=CH₂ | H | OCH₃ | |
| SO₂CH₂CH=CH₂ | H | OCH₃ | |
| SCH₂CH=CHCH₃ | H | OCH₃ | |
| SOCH₂CH=CHCH₃ | H | OCH₃ | |
| SO₂CH₂CH=CHCH₃ | H | OCH₃ | |
| SCH₂CH(cyclopropyl) | H | OCH₃ | |
| SOCH₂CH(cyclopropyl) | H | OCH₃ | |
| SO₂CH₂CH(cyclopropyl) | H | OCH₃ | |
| SCH₃ | H | C₂H₅ | |
| SOCH₃ | H | C₂H₅ | |
| SO₂CH₃ | H | C₂H₅ | |
| SC₂H₅ | H | C₂H₅ | |
| SOC₂H₅ | H | C₂H₅ | |
| SO₂C₂H₅ | H | C₂H₅ | |
| S(CH₂)₂CH₃ | H | C₂H₅ | |
| SO(CH₂)₂CH₃ | H | C₂H₅ | |
| SO₂(CH₂)₂CH₃ | H | C₂H₅ | |
| SCH(CH₃)₂ | H | C₂H₅ | |
| SOCH(CH₃)₂ | H | C₂H₅ | |
| SO₂CH(CH₃)₂ | H | C₂H₅ | |
| S(CH₂)₃CH₃ | H | C₂H₅ | |
| SO(CH₂)₃CH₃ | H | C₂H₅ | |
| SO₂(CH₂)₃CH₃ | H | C₂H₅ | |
| SCH₂CH(CH₃)₂ | H | C₂H₅ | |
| SOCH₂CH(CH₃)₂ | H | C₂H₅ | |
| SO₂CH₂CH(CH₃)₂ | H | C₂H₅ | |
| SCH(CH₃)CH₂CH₃ | H | C₂H₅ | |
| SOCH(CH₃)CH₂CH₃ | H | C₂H₅ | |
| SO₂CH(CH₃)CH₂CH₃ | H | C₂H₅ | |
| SC(CH₃)₃ | H | C₂H₅ | |
| SOC(CH₃)₃ | H | C₂H₅ | |
| SO₂C(CH₃)₃ | H | C₂H₅ | |
| SCH₂CH=CH₂ | H | C₂H₅ | |
| SOCH₂CH=CH₂ | H | C₂H₅ | |
| SO₂CH₂CH=CH₂ | H | C₂H₅ | |
| SCH₂CH=CHCH₃ | H | C₂H₅ | |
| SOCH₂CH=CHCH₃ | H | C₂H₅ | |

TABLE III-continued

Structure: phenyl ring with H, R1, R2 substituents, connected via SO2NHC(O)NH to a pyridine ring with X and N(CH3)2 substituents.

| R1 | R2 | X | m.p. (°C.) |
|---|---|---|---|
| SO2CH2CH=CHCH3 | H | C2H5 | |
| SCH2CH(CH2)(CH2) [cyclopropyl] | H | C2H5 | |
| SOCH2CH(CH2)(CH2) [cyclopropyl] | H | C2H5 | |
| SO2CH2CH(CH2)(CH2) [cyclopropyl] | H | C2H5 | |
| SCH3 | H | OC2H5 | |
| SOCH3 | H | OC2H5 | |
| SO2CH3 | H | OC2H5 | |
| SC2H5 | H | OC2H5 | |
| SOC2H5 | H | OC2H5 | |
| SO2C2H5 | H | OC2H5 | |
| S(CH2)2CH3 | H | OC2H5 | |
| SO(CH2)2CH3 | H | OC2H5 | |
| SO2(CH2)2CH3 | H | OC2H5 | |
| SCH(CH3)2 | H | OC2H5 | |
| SOCH(CH3)2 | H | OC2H5 | |
| SO2CH(CH3)2 | H | OC2H5 | |
| S(CH2)3CH3 | H | OC2H5 | |
| SO(CH2)3CH3 | H | OC2H5 | |
| SO2(CH2)3CH3 | H | OC2H5 | |
| SCH2CH(CH3)2 | H | OC2H5 | |
| SOCH2CH(CH3)2 | H | OC2H5 | |
| SO2CH2CH(CH3)2 | H | OC2H5 | |
| SCH(CH3)CH2CH3 | H | OC2H5 | |
| SOCH(CH3)CH2CH3 | H | OC2H5 | |
| SO2CH(CH3)CH2CH3 | H | OC2H5 | |
| SC(CH3)3 | H | OC2H5 | |
| SOC(CH3)3 | H | OC2H5 | |
| SO2C(CH3)3 | H | OC2H5 | |
| SCH2CH=CH2 | H | OC2H5 | |
| SOCH2CH=CH2 | H | OC2H5 | |
| SO2CH2CH=CH2 | H | OC2H5 | |
| SCH2CH=CHCH3 | H | OC2H5 | |
| SOCH2CH=CHCH3 | H | OC2H5 | |
| SO2CH2CH=CHCH3 | H | OC2H5 | |
| SCH2CH(CH2)(CH2) [cyclopropyl] | H | OC2H5 | |
| SOCH2CH(CH2)(CH2) [cyclopropyl] | H | OC2H5 | |
| SO2CH2CH(CH2)(CH2) [cyclopropyl] | H | OC2H5 | |
| SCH3 | H | CH2OCH3 | |
| SOCH3 | H | CH2OCH3 | |
| SO2CH3 | H | CH2OCH3 | |
| SC2H5 | H | CH2OCH3 | |
| SOC2H5 | H | CH2OCH3 | |
| SO2C2H5 | H | CH2OCH3 | |
| S(CH2)2CH3 | H | CH2OCH3 | |
| SO(CH2)2CH3 | H | CH2OCH3 | |
| SO2(CH2)2CH3 | H | CH2OCH3 | |
| SCH(CH3)2 | H | CH2OCH3 | |
| SOCH(CH3)2 | H | CH2OCH3 | |
| SO2CH(CH3)2 | H | CH2OCH3 | |
| S(CH2)3CH3 | H | CH2OCH3 | |
| SO(CH2)3CH3 | H | CH2OCH3 | |
| SO2(CH2)3CH3 | H | CH2OCH3 | |
| SCH2CH(CH3)2 | H | CH2OCH3 | |
| SOCH2CH(CH3)2 | H | CH2OCH3 | |
| SO2CH2CH(CH3)2 | H | CH2OCH3 | |
| SCH(CH3)CH2CH3 | H | CH2OCH3 | |
| SOCH(CH3)CH2CH3 | H | CH2OCH3 | |
| SO2CH(CH3)CH2CH3 | H | CH2OCH3 | |
| SC(CH3)3 | H | CH2OCH3 | |
| SOC(CH3)3 | H | CH2OCH3 | |
| SO2C(CH3)3 | H | CH2OCH3 | |
| SCH2CH=CH2 | H | CH2OCH3 | |
| SOCH2CH=CH2 | H | CH2OCH3 | |
| SO2CH2CH=CH2 | H | CH2OCH3 | |
| SCH2CH=CHCH3 | H | CH2OCH3 | |
| SOCH2CH=CHCH3 | H | CH2OCH3 | |
| SO2CH2CH=CHCH3 | H | CH2OCH3 | |
| SCH2CH(CH2)(CH2) [cyclopropyl] | H | CH2OCH3 | |
| SOCH2CH(CH2)(CH2) [cyclopropyl] | H | CH2OCH3 | |
| SO2CH2CH(CH2)(CH2) [cyclopropyl] | H | CH2OCH3 | |
| SO2CH3 | 3-CH3 | CH3 | |
| SO2CH3 | 5-CF3 | CH3 | |
| SO2CH3 | 5-Cl | OCH3 | |
| SO2CH3 | 5-OCH3 | C2H5 | |
| SO2CH3 | 5-NO2 | OC2H5 | |
| SO2CH3 | 6-CH3 | CH2OCH3 | |
| SC2H5 | 5-CH3 | CH3 | |
| SOC2H5 | 5-CF3 | OCH3 | |
| SO2C2H5 | 5-Cl | C2H5 | |
| SO2C2H5 | 6-Br | OC2H5 | |
| SO2(CH2)2CH3 | 3-CH3 | CH3 | |
| SO2(CH2)2CH3 | 3-Br | OCH3 | |
| SO2(CH2)2CH3 | 5-CH3 | C2H5 | |
| SO2(CH2)2CH3 | 5-CF3 | OC2H5 | |
| SO2(CH2)2CH3 | 5-OCH3 | CH3 | |
| SO2(CH2)2CH3 | 5-Cl | CH2OCH3 | |
| SO2(CH2)2CH3 | 6-NO2 | CH3 | |
| SO2(CH2)2CH3 | 6-CH3 | C2H5 | |
| S(CH2)3CH3 | 5-CH3 | OC2H5 | |
| SO(CH2)3CH3 | 5-CF3 | OCH3 | |
| SO2CH2CH=CH2 | 3-Br | CH3 | |
| SO2CH2CH=CH2 | 3-Cl | OCH3 | |
| SO2CH2CH=CH2 | 5-CH3 | OC2H5 | |
| SO2CH2CH=CH2 | 5-OCH3 | C2H5 | |
| SO2CH2CHCH3 | 5-CF3 | C2H5 | |
| SO2CH2CH=CH2 | 6-NO2 | CH2OCH3 | |
| SCH2C(CH3)=CH2 | 5-CF3 | OCH3 | |
| SOCH2CH(CH2)(CH2) [cyclopropyl] | 3-CH3 | OC2H5 | |

TABLE III-continued

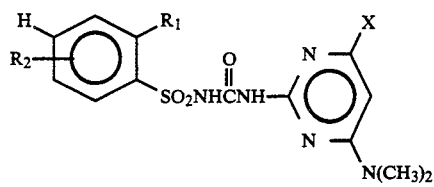

| R₁ | R₂ | X | m.p. (°C.) |
|---|---|---|---|
| SO₂CH₂CH(CH₂CH₂ cyclopropyl) | 5-Cl | CH₂OCH₃ | |

TABLE IV

| R₁ | R₂ | X | m.p. (°C.) |
|---|---|---|---|
| SCH₃ | H | CH₃ | |
| SOCH₃ | H | CH₃ | |
| SO₂CH₃ | H | CH₃ | 139–141° |
| SC₂H₅ | H | CH₃ | |
| SOC₂H₅ | H | CH₃ | |
| SO₂C₂H₅ | H | CH₃ | |
| S(CH₂)₂CH₃ | H | CH₃ | |
| SO(CH₂)₂CH₃ | H | CH₃ | |
| SO₂(CH₂)₂CH₃ | H | CH₃ | |
| SCH(CH₃)₂ | H | CH₃ | |
| SOCH(CH₃)₂ | H | CH₃ | |
| SO₂CH(CH₃)₂ | H | CH₃ | |
| S(CH₂)₃CH₃ | H | CH₃ | |
| SO(CH₂)₃CH₃ | H | CH₃ | |
| SO₂(CH₂)₃CH₃ | H | CH₃ | |
| SCH₂CH(CH₃)₂ | H | CH₃ | |
| SOCH₂CH(CH₃)₂ | H | CH₃ | |
| SO₂CH₂CH(CH₃)₂ | H | CH₃ | |
| SCH(CH₃)CH₂CH₃ | H | CH₃ | |
| SOCH(CH₃)CH₂CH₃ | H | CH₃ | |
| SO₂CH(CH₃)CH₂CH₃ | H | CH₃ | |
| SC(CH₃)₃ | H | CH₃ | |
| SOC(CH₃)₃ | H | CH₃ | |
| SO₂C(CH₃)₃ | H | CH₃ | |
| SCH₂CH=CH₂ | H | CH₃ | |
| SOCH₂CH=CH₂ | H | CH₃ | |
| SO₂CH₂CH=CH₂ | H | CH₃ | |
| SCH₂CH=CHCH₃ | H | CH₃ | |
| SOCH₂CH=CHCH₃ | H | CH₃ | |
| SO₂CH₂CH=CHCH₃ | H | CH₃ | |
| SCH₂CH(cyclopropyl) | H | CH₃ | |
| SOCH₂CH(cyclopropyl) | H | CH₃ | |
| SO₂CH₂CH(cyclopropyl) | H | CH₃ | |
| SCH₃ | H | OCH₃ | |
| SOCH₃ | H | OCH₃ | |
| SO₂CH₃ | H | OCH₃ | 192–195° |
| SC₂H₅ | H | OCH₃ | |
| SOC₂H₅ | H | OCH₃ | |
| SO₂C₂H₅ | H | OCH₃ | 189–192° |

TABLE IV-continued

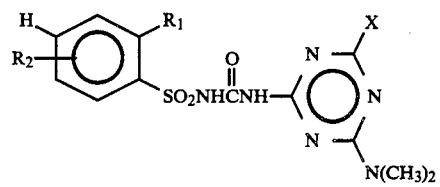

| R₁ | R₂ | X | m.p. (°C.) |
|---|---|---|---|
| S(CH₂)₂CH₃ | H | OCH₃ | |
| SO(CH₂)₂CH₃ | H | OCH₃ | |
| SO₂(CH₂)₂CH₃ | H | OCH₃ | 208–210° |
| SCH(CH₃)₂ | H | OCH₃ | |
| SOCH(CH₃)₂ | H | OCH₃ | |
| SO₂CH(CH₃)₂ | H | OCH₃ | |
| S(CH₂)₃CH₃ | H | OCH₃ | |
| SO(CH₂)₃CH₃ | H | OCH₃ | |
| SO₂(CH₂)₃CH₃ | H | OCH₃ | |
| SCH₂CH(CH₃)₂ | H | OCH₃ | |
| SOCH₂CH(CH₃)₂ | H | OCH₃ | |
| SO₂CH₂CH(CH₃)₂ | H | OCH₃ | |
| SCH(CH₃)CH₂CH₃ | H | OCH₃ | |
| SOCH(CH₃)CH₂CH₃ | H | OCH₃ | |
| SO₂CH(CH₃)CH₂CH₃ | H | OCH₃ | |
| SC(CH₃)₃ | H | OCH₃ | |
| SOC(CH₃)₃ | H | OCH₃ | |
| SO₂C(CH₃)₃ | H | OCH₃ | |
| SCH₂CH=CH₂ | H | OCH₃ | |
| SOCH₂CH=CH₂ | H | OCH₃ | |
| SO₂CH₂CH=CH₂ | H | OCH₃ | |
| SCH₂CH=CHCH₃ | H | OCH₃ | |
| SOCH₂CH=CHCH₃ | H | OCH₃ | |
| SO₂CH₂CH=CHCH₃ | H | OCH₃ | |
| SCH₂CH(cyclopropyl) | H | OCH₃ | |
| SOCH₂CH(cyclopropyl) | H | OCH₃ | |
| SO₂CH₂CH(cyclopropyl) | H | OCH₃ | |
| SCH₃ | H | C₂H₅ | |
| SOCH₃ | H | C₂H₅ | |
| SO₂CH₃ | H | C₂H₅ | |
| SC₂H₅ | H | C₂H₅ | |
| SOC₂H₅ | H | C₂H₅ | |
| SO₂C₂H₅ | H | C₂H₅ | |
| S(CH₂)₂CH₃ | H | C₂H₅ | |
| SO(CH₂)₂CH₃ | H | C₂H₅ | |
| SO₂(CH₂)₂CH₃ | H | C₂H₅ | |
| SCH(CH₃)₂ | H | C₂H₅ | |
| SOCH(CH₃)₂ | H | C₂H₅ | |
| SO₂CH(CH₃)₂ | H | C₂H₅ | |
| S(CH₂)₃CH₃ | H | C₂H₅ | |
| SO(CH₂)₃CH₃ | H | C₂H₅ | |
| SO₂(CH₂)₃CH₃ | H | C₂H₅ | |
| SCH₂CH(CH₃)₂ | H | C₂H₅ | |
| SOCH₂CH(CH₃)₂ | H | C₂H₅ | |
| SO₂CH₂CH(CH₃)₂ | H | C₂H₅ | |
| SCH(CH₃)CH₂CH₃ | H | C₂H₅ | |
| SOCH(CH₃)CH₂CH₃ | H | C₂H₅ | |
| SO₂CH(CH₃)CH₂CH₃ | H | C₂H₅ | |
| SC(CH₃)₃ | H | C₂H₅ | |
| SOC(CH₃)₃ | H | C₂H₅ | |
| SO₂C(CH₃)₃ | H | C₂H₅ | |
| SCH₂CH=CH₂ | H | C₂H₅ | |
| SOCH₂CH=CH₂ | H | C₂H₅ | |
| SO₂CH₂CH=CH₂ | H | C₂H₅ | |
| SCH₂CH=CHCH₃ | H | C₂H₅ | |
| SOCH₂CH=CHCH₃ | H | C₂H₅ | |
| SO₂CH₂CH=CHCH₃ | H | C₂H₅ | |

TABLE IV-continued

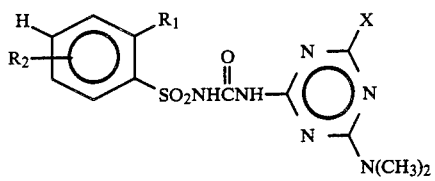

| R₁ | R₂ | X | m.p. (°C.) |
|---|---|---|---|
| SCH₂CH(CH₂)(CH₂) [cyclopropyl] | H | C₂H₅ | |
| SOCH₂CH(CH₂)(CH₂) | H | C₂H₅ | |
| SO₂CH₂CH(CH₂)(CH₂) | H | C₂H₅ | |
| SCH₃ | H | OC₂H₅ | |
| SOCH₃ | H | OC₂H₅ | |
| SO₂CH₃ | H | OC₂H₅ | |
| SC₂H₅ | H | OC₂H₅ | |
| SOC₂H₅ | H | OC₂H₅ | |
| SO₂C₂H₅ | H | OC₂H₅ | |
| S(CH₂)₂CH₃ | H | OC₂H₅ | |
| SO(CH₂)₂CH₃ | H | OC₂H₅ | |
| SO₂(CH₂)₂CH₃ | H | OC₂H₅ | 91-93° (d) |
| SCH(CH₃)₂ | H | OC₂H₅ | |
| SOCH(CH₃)₂ | H | OC₂H₅ | |
| SO₂CH(CH₃)₂ | H | OC₂H₅ | |
| S(CH₂)₃CH₃ | H | OC₂H₅ | |
| SO(CH₂)₃CH₃ | H | OC₂H₅ | |
| SO₂(CH₂)₃CH₃ | H | OC₂H₅ | |
| SCH₂CH(CH₃)₂ | H | OC₂H₅ | |
| SOCH₂CH(CH₃)₂ | H | OC₂H₅ | |
| SO₂CH₂CH(CH₃)₂ | H | OC₂H₅ | |
| SCH(CH₃)CH₂CH₃ | H | OC₂H₅ | |
| SOCH(CH₃)CH₂CH₃ | H | OC₂H₅ | |
| SO₂CH(CH₃)CH₂CH₃ | H | OC₂H₅ | |
| SC(CH₃)₃ | H | OC₂H₅ | |
| SOC(CH₃)₃ | H | OC₂H₅ | |
| SO₂C(CH₃)₃ | H | OC₂H₅ | |
| SCH₂CH=CH₂ | H | OC₂H₅ | |
| SOCH₂CH=CH₂ | H | OC₂H₅ | |
| SO₂CH₂CH=CH₂ | H | OC₂H₅ | |
| SCH₂CH=CHCH₃ | H | OC₂H₅ | |
| SOCH₂CH=CHCH₃ | H | OC₂H₅ | |
| SO₂CH₂CH=CHCH₃ | H | OC₂H₅ | |
| SCH₂CH(CH₂)(CH₂) | H | OC₂H₅ | |
| SOCH₂CH(CH₂)(CH₂) | H | OC₂H₅ | |
| SO₂CH₂CH(CH₂)(CH₂) | H | OC₂H₅ | |
| SCH₃ | H | CH₂OCH₃ | |
| SOCH₃ | H | CH₂OCH₃ | |
| SO₂CH₃ | H | CH₂OCH₃ | |
| SC₂H₅ | H | CH₂OCH₃ | |
| SOC₂H₅ | H | CH₂OCH₃ | |
| SO₂C₂H₅ | H | CH₂OCH₃ | |
| S(CH₂)₂CH₃ | H | CH₂OCH₃ | |
| SO(CH₂)₂CH₃ | H | CH₂OCH₃ | |
| SO₂(CH₂)₂CH₃ | H | CH₂OCH₃ | |
| SCH(CH₃)₂ | H | CH₂OCH₃ | |
| SOCH(CH₃)₂ | H | CH₂OCH₃ | |
| SO₂CH(CH₃)₂ | H | CH₂OCH₃ | |
| S(CH₂)₃CH₃ | H | CH₂OCH₃ | |
| SO(CH₂)₃CH₃ | H | CH₂OCH₃ | |
| SO₂(CH₂)₃CH₃ | H | CH₂OCH₃ | |
| SCH₂CH(CH₃)₂ | H | CH₂OCH₃ | |
| SOCH₂CH(CH₃)₂ | H | CH₂OCH₃ | |
| SO₂CH₂CH(CH₃)₂ | H | CH₂OCH₃ | |
| SCH(CH₃)CH₂CH₃ | H | CH₂OCH₃ | |
| SOCH(CH₃)CH₂CH₃ | H | CH₂OCH₃ | |
| SO₂CH(CH₃)CH₂CH₃ | H | CH₂OCH₃ | |
| SC(CH₃)₃ | H | CH₂OCH₃ | |
| SOC(CH₃)₃ | H | CH₂OCH₃ | |
| SO₂C(CH₃)₃ | H | CH₂OCH₃ | |
| SCH₂CH=CH₂ | H | CH₂OCH₃ | |
| SOCH₂CH=CH₂ | H | CH₂OCH₃ | |
| SO₂CH₂CH=CH₂ | H | CH₂OCH₃ | |
| SCH₂CH=CHCH₃ | H | CH₂OCH₃ | |
| SOCH₂CH=CHCH₃ | H | CH₂OCH₃ | |
| SO₂CH₂CH=CHCH₃ | H | CH₂OCH₃ | |
| SCH₂CH(CH₂)(CH₂) | H | CH₂OCH₃ | |
| SOCH₂CH(CH₂)(CH₂) | H | CH₂OCH₃ | |
| SO₂CH₂CH(CH₂)(CH₂) | H | CH₂OCH₃ | |
| SO₂CH₃ | 3-CH₃ | CH₃ | |
| SO₂CH₃ | 5-CF₃ | CH₃ | |
| SO₂CH₃ | 5-Cl | OCH₃ | |
| SO₂CH₃ | 5-OCH₃ | C₂H₅ | |
| SO₂CH₃ | 5-NO₂ | OC₂H₅ | |
| SO₂CH₃ | 6-CH₃ | CH₂OCH₃ | |
| SC₂H₅ | 5-CH₃ | CH₃ | |
| SOC₂H₅ | 5-CF₃ | OCH₃ | |
| SO₂C₂H₅ | 5-Cl | C₂H₅ | |
| SO₂C₂H₅ | 6-Br | OC₂H₅ | |
| SO₂(CH₂)₂CH₃ | 3-CH₃ | CH₃ | |
| SO₂(CH₂)₂CH₃ | 3-Br | OCH₃ | |
| SO₂(CH₂)₂CH₃ | 5-CH₃ | C₂H₅ | |
| SO₂(CH₂)₂CH₃ | 5-CF₃ | OC₂H₅ | |
| SO₂(CH₂)₂CH₃ | 5-OCH₃ | CH₃ | |
| SO₂(CH₂)₂CH₃ | 5-Cl | CH₂OCH₃ | |
| SO₂(CH₂)₂CH₃ | 6-NO₂ | CH₃ | |
| SO₂(CH₂)₂CH₃ | 6-CH₃ | C₂H₅ | |
| S(CH₂)₃CH₃ | 5-CH₃ | OC₂H₅ | |
| SO(CH₂)₃CH₃ | 5-CF₃ | OCH₃ | |
| SO₂CH₂CH=CH₂ | 3-Br | CH₃ | |
| SO₂CH₂CH=CH₂ | 3-Cl | OCH₃ | |
| SO₂CH₂CH=CH₂ | 5-CH₃ | OC₂H₅ | |
| SO₂CH₂CH=CH₂ | 5-OCH₃ | C₂H₅ | |
| SO₂CH₂CHCH₃ | 5-CF₃ | C₂H₅ | |
| SO₂CH₂CH=CH₂ | 6-NO₂ | CH₂OCH₃ | |
| SCH₂C(CH₃)=CH₂ | 5-CF₃ | OCH₃ | |
| SOCH₂CH(CH₂)(CH₂) | 3-CH₃ | OC₂H₅ | |

TABLE IV-continued

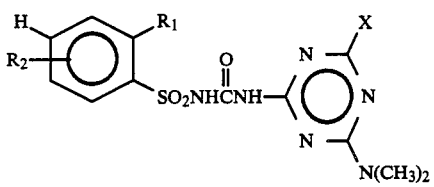

| R₁ | R₂ | X | m.p. (°C.) |
|---|---|---|---|
| SO₂CH₂CH(CH₂CH₂ cyclopropyl) | 5-Cl | CH₂OCH₃ | |

TABLE V

| R₁ | R₂ | X | m.p. (°C.) |
|---|---|---|---|
| SCH₃ | H | CH₃ | |
| SOCH₃ | H | CH₃ | |
| SO₂CH₃ | H | CH₃ | 188–208° |
| SC₂H₅ | H | CH₃ | |
| SOC₂H₅ | H | CH₃ | |
| SO₂C₂H₅ | H | CH₃ | |
| S(CH₂)₂CH₃ | H | CH₃ | |
| SO(CH₂)₂CH₃ | H | CH₃ | |
| SO₂(CH₂)₂CH₃ | H | CH₃ | |
| SCH(CH₃)₂ | H | CH₃ | |
| SOCH(CH₃)₂ | H | CH₃ | |
| SO₂CH(CH₃)₂ | H | CH₃ | |
| S(CH₂)₃CH₃ | H | CH₃ | |
| SO(CH₂)₃CH₃ | H | CH₃ | |
| SO₂(CH₂)₃CH₃ | H | CH₃ | |
| SCH₂CH(CH₃)₂ | H | CH₃ | |
| SOCH₂CH(CH₃)₂ | H | CH₃ | |
| SO₂CH₂CH(CH₃)₂ | H | CH₃ | |
| SCH(CH₃)CH₂CH₃ | H | CH₃ | |
| SOCH(CH₃)CH₂CH₃ | H | CH₃ | |
| SO₂CH(CH₃)CH₂CH₃ | H | CH₃ | |
| SC(CH₃)₃ | H | CH₃ | |
| SOC(CH₃)₃ | H | CH₃ | |
| SO₂C(CH₃)₃ | H | CH₃ | |
| SCH₂CH=CH₂ | H | CH₃ | |
| SOCH₂CH=CH₂ | H | CH₃ | |
| SO₂CH₂CH=CH₂ | H | CH₃ | |
| SCH₂CH=CHCH₃ | H | CH₃ | |
| SOCH₂CH=CHCH₃ | H | CH₃ | |
| SO₂CH₂CH=CHCH₃ | H | CH₃ | |
| SCH₂CH(cyclopropyl) | H | CH₃ | |
| SOCH₂CH(cyclopropyl) | H | CH₃ | |
| SO₂CH₂CH(cyclopropyl) | H | CH₃ | |
| SCH₃ | H | OCH₃ | |
| SOCH₃ | H | OCH₃ | |
| SO₂CH₃ | H | OCH₃ | |
| SC₂H₅ | H | OCH₃ | |
| SOC₂H₅ | H | OCH₃ | |
| SO₂C₂H₅ | H | OCH₃ | 208–221° |

TABLE V-continued

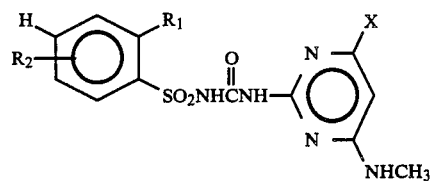

| R₁ | R₂ | X | m.p. (°C.) |
|---|---|---|---|
| S(CH₂)₂CH₃ | H | OCH₃ | 159–160° |
| SO(CH₂)₂CH₃ | H | OCH₃ | |
| SO₂(CH₂)₂CH₃ | H | OCH₃ | 217–220° |
| SCH(CH₃)₂ | H | OCH₃ | |
| SOCH(CH₃)₂ | H | OCH₃ | |
| SO₂CH(CH₃)₂ | H | OCH₃ | |
| S(CH₂)₃CH₃ | H | OCH₃ | |
| SO(CH₂)₃CH₃ | | | |
| SO₂(CH₂)₃CH₃ | H | OCH₃ | |
| SCH₂CH(CH₃)₂ | H | OCH₃ | |
| SOCH₂CH(CH₃)₂ | H | OCH₃ | |
| SO₂CH₂CH(CH₃)₂ | H | OCH₃ | |
| SCH(CH₃)CH₂CH₃ | H | OCH₃ | |
| SOCH(CH₃)CH₂CH₃ | H | OCH₃ | |
| SO₂CH(CH₃)CH₂CH₃ | H | OCH₃ | |
| SO₂CH(CH₃)CH₂CH₃ | H | OCH₃ | |
| SC(CH₃)₃ | H | OCH₃ | |
| SOC(CH₃)₃ | H | OCH₃ | |
| SO₂C(CH₃)₃ | H | OCH₃ | |
| SCH₂CH=CH₂ | H | OCH₃ | |
| SOCH₂CH=CH₂ | H | OCH₃ | |
| SO₂CH₂CH=CH₂ | H | OCH₃ | |
| SCH₂CH=CHCH₃ | H | OCH₃ | |
| SOCH₂CH=CHCH₃ | H | OCH₃ | |
| SO₂CH₂CH=CHCH₃ | H | OCH₃ | |
| SCH₂CH(cyclopropyl) | H | OCH₃ | |
| SOCH₂CH(cyclopropyl) | H | OCH₃ | |
| SO₂CH₂CH(cyclopropyl) | H | OCH₃ | |
| S(CH₂)₃CH₃ | H | C₂H₅ | |
| SO(CH₂)₃CH₃ | H | C₂H₅ | |
| SO₂(CH₂)₃CH₃ | H | C₂H₅ | |
| SCH₂CH(CH₃)₂ | H | C₂H₅ | |
| SOCH₂CH(CH₃)₂ | H | C₂H₅ | |
| SO₂CH₂CH(CH₃)₂ | H | C₂H₅ | |
| SCH(CH₃)CH₂CH₃ | H | C₂H₅ | |
| SOCH(CH₃)CH₂CH₃ | H | C₂H₅ | |
| SO₂CH(CH₃)CH₂CH₃ | H | C₂H₅ | |
| SC(CH₃)₃ | H | C₂H₅ | |
| SOC(CH₃)₃ | H | C₂H₅ | |
| SO₂C(CH₃)₃ | H | C₂H₅ | |
| SCH₂CH=CH₂ | H | C₂H₅ | |
| SOCH₂CH=CH₂ | H | C₂H₅ | |
| SO₂CH₂CH=CH₂ | H | C₂H₅ | |
| SCH₂CH=CHCH₃ | H | C₂H₅ | |
| SOCH₂CH=CHCH₃ | H | C₂H₅ | |
| SO₂CH₂CH=CHCH₃ | H | C₂H₅ | |
| SCH₂CH(cyclopropyl) | H | C₂H₅ | |
| SOCH₂CH(cyclopropyl) | H | C₂H₅ | |

TABLE V-continued

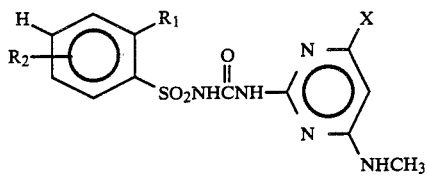

| R₁ | R₂ | X | m.p. (°C.) |
|---|---|---|---|
| SO₂CH₂CH(CH₂)(CH₂) [cyclopropyl] | H | C₂H₅ | |
| SCH₃ | H | OC₂H₅ | |
| SOCH₃ | H | OC₂H₅ | |
| SO₂CH₃ | H | OC₂H₅ | |
| SC₂H₅ | H | OC₂H₅ | |
| SOC₂H₅ | H | OC₂H₅ | |
| SO₂C₂H₅ | H | OC₂H₅ | 175–178° |
| S(CH₂)₂CH₃ | H | OC₂H₅ | |
| SO(CH₂)₂CH₃ | H | OC₂H₅ | |
| SO₂(CH₂)₂CH₃ | H | OC₂H₅ | |
| SCH(CH₃)₂ | H | OC₂H₅ | |
| SOCH(CH₃)₂ | H | OC₂H₅ | |
| SO₂CH(CH₃)₂ | H | OC₂H₅ | |
| S(CH₂)₃CH₃ | H | OC₂H₅ | |
| SO(CH₂)₃CH₃ | H | OC₂H₅ | |
| SO₂(CH₂)₃CH₃ | H | OC₂H₅ | |
| SCH₂CH(CH₃)₂ | H | OC₂H₅ | |
| SOCH₂CH(CH₃)₂ | H | OC₂H₅ | |
| SO₂CH₂CH(CH₃)₂ | H | OC₂H₅ | |
| SCH(CH₃)CH₂CH₃ | H | OC₂H₅ | |
| SOCH(CH₃)CH₂CH₃ | H | OC₂H₅ | |
| SO₂CH(CH₃)CH₂CH₃ | H | OC₂H₅ | |
| SC(CH₃)₃ | H | OC₂H₅ | |
| SOC(CH₃)₃ | H | OC₂H₅ | |
| SO₂C(CH₃)₃ | H | OC₂H₅ | |
| SCH₂CH=CH₂ | H | OC₂H₅ | |
| SOCH₂CH=CH₂ | H | OC₂H₅ | |
| SO₂CH₂CH=CH₂ | H | OC₂H₅ | |
| SCH₂CH=CHCH₃ | H | OC₂H₅ | |
| SOCH₂CH=CHCH₃ | H | OC₂H₅ | |
| SO₂CH₂CH=CHCH₃ | H | OC₂H₅ | |
| SCH₂CH(cyclopropyl) | H | OC₂H₅ | |
| SOCH₂CH(cyclopropyl) | H | OC₂H₅ | |
| SO₂CH₂CH(cyclopropyl) | H | OC₂H₅ | |
| S(CH₂)₃CH₃ | H | CH₂OCH₃ | |
| SO(CH₂)₃CH₃ | H | CH₂OCH₃ | |
| SO₂(CH₂)₃CH₃ | H | CH₂OCH₃ | |
| SCH₂CH(CH₃)₂ | H | CH₂OCH₃ | |
| SOCH₂CH(CH₃)₂ | H | CH₂OCH₃ | |
| SO₂CH₂CH(CH₃)₂ | H | CH₂OCH₃ | |
| SCH(CH₃)CH₂CH₃ | H | CH₂OCH₃ | |
| SOCH(CH₃)CH₂CH₃ | H | CH₂OCH₃ | |
| SO₂CH(CH₃)CH₂CH₃ | H | CH₂OCH₃ | |
| SC(CH₃)₃ | H | CH₂OCH₃ | |
| SOC(CH₃)₃ | H | CH₂OCH₃ | |
| SO₂C(CH₃)₃ | H | CH₂OCH₃ | |
| SCH₂CH=CH₂ | H | CH₂OCH₃ | |
| SOCH₂CH=CH₂ | H | CH₂OCH₃ | |
| SO₂CH₂CH=CH₂ | H | CH₂OCH₃ | |
| SCH₂CH=CHCH₃ | H | CH₂OCH₃ | |
| SOCH₂CH=CHCH₃ | H | CH₂OCH₃ | |
| SO₂CH₂CH=CHCH₃ | H | CH₂OCH₃ | |

TABLE V-continued

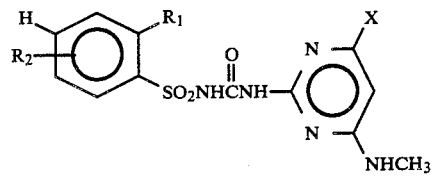

| R₁ | R₂ | X | m.p. (°C.) |
|---|---|---|---|
| SCH₂CH(cyclopropyl) | H | CH₂OCH₃ | |
| SOCH₂CH(cyclopropyl) | H | CH₂OCH₃ | |
| SO₂CH₂CH(cyclopropyl) | H | CH₂OCH₃ | |
| SO₂CH₃ | 3-CH₃ | CH₃ | |
| SO₂CH₃ | 5-CF₃ | CH₃ | |
| SO₂CH₃ | 5-Cl | OCH₃ | |
| SO₂CH₃ | 5-OCH₃ | OCH₃ | |
| SO₂CH₃ | 5-NO₂ | OC₂H₅ | |
| SO₂CH₃ | 6-CH₃ | OCH₃ | |
| SC₂H₅ | 5-CH₃ | CH₃ | |
| SOC₂H₅ | 5-CF₃ | OCH₃ | |
| SO₂C₂H₅ | 5-Cl | OCH₃ | |
| SO₂C₂H₅ | 6-Br | OC₂H₅ | |
| SO₂(CH₂)₂CH₃ | 3-CH₃ | CH₃ | |
| SO₂(CH₂)₂CH₃ | 3-Br | OCH₃ | |
| SO₂(CH₂)₂CH₃ | 5-CH₃ | OCH₃ | |
| SO₂(CH₂)₂CH₃ | 5-CF₃ | OC₂H₅ | |
| SO₂(CH₂)₂CH₃ | 5-OCH₃ | CH₃ | |
| SO₂(CH₂)₂CH₃ | 5-Cl | OCH₃ | |
| SO₂(CH₂)₂CH₃ | 6-NO₂ | CH₃ | |
| SO₂(CH₂)₂CH₃ | 6-CH₃ | OCH₃ | |
| S(CH₂)₃CH₃ | 5-CH₃ | OC₂H₅ | |
| SO(CH₂)₃CH₃ | 5-CF₃ | OCH₃ | |
| SO₂CH₂CH=CH₂ | 3-Br | CH₃ | |
| SO₂CH₂CH=CH₂ | 3-Cl | OCH₃ | |
| SO₂CH₂CH=CH₂ | 5-CH₃ | OC₂H₅ | |
| SO₂CH₂CH=CH₂ | 5-OCH₃ | C₂H₅ | |
| SO₂CH₂CH=CH₂ | 5-CF₃ | C₂H₅ | |
| SO₂CH₂CH=CH₂ | 6-NO₂ | CH₂OCH₃ | |
| SCH₂C(CH₃)=CH₂ | 5-CF₃ | OCH₃ | |
| SO₂CH₂CH(cyclopropyl) | 3-CH₃ | OC₂H₅ | |
| SO₂CH₂CH(cyclopropyl) | 5-Cl | CH₂OCH₃ | |

TABLE VI

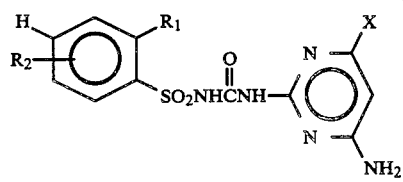

| R₁ | R₂ | X | m.p. (°C.) |
|---|---|---|---|
| SCH₃ | H | CH₃ | |
| SOCH₃ | H | CH₃ | |
| SO₂CH₃ | H | CH₃ | |
| SC₂H₅ | H | CH₃ | |

TABLE VI-continued

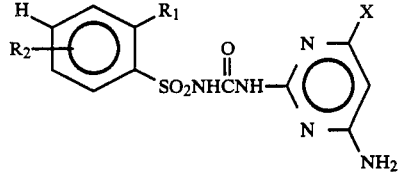

| R₁ | R₂ | X | m.p. (°C.) |
|---|---|---|---|
| SOC₂H₅ | H | CH₃ | |
| SO₂C₂H₅ | H | CH₃ | |
| S(CH₂)₂CH₃ | H | CH₃ | |
| SO(CH₂)₂CH₃ | H | CH₃ | |
| SO₂(CH₂)₂CH₃ | H | CH₃ | |
| SCH(CH₃)₂ | H | CH₃ | |
| SOCH(CH₃)₂ | H | CH₃ | |
| SO₂CH(CH₃)₂ | H | CH₃ | |
| S(CH₂)₃CH₃ | H | CH₃ | |
| SO(CH₂)₃CH₃ | H | CH₃ | |
| SO₂(CH₂)₃CH₃ | H | CH₃ | |
| SCH₂CH(CH₃)₂ | H | CH₃ | |
| SOCH₂CH(CH₃)₂ | H | CH₃ | |
| SO₂CH₂CH(CH₃)₂ | H | CH₃ | |
| SCH(CH₃)CH₂CH₃ | H | CH₃ | |
| SOCH(CH₃)CH₂CH₃ | H | CH₃ | |
| SO₂CH(CH₃)CH₂CH₃ | H | CH₃ | |
| SC(CH₃)₃ | H | CH₃ | |
| SOC(CH₃)₃ | H | CH₃ | |
| SO₂C(CH₃)₃ | H | CH₃ | |
| SCH₂CH=CH₂ | H | CH₃ | |
| SOCH₂CH=CH₂ | H | CH₃ | |
| SO₂CH₂CH=CH₂ | H | CH₃ | |
| SCH₂CH=CHCH₃ | H | CH₃ | |
| SOCH₂CH=CHCH₃ | H | CH₃ | |
| SO₂CH₂CH=CHCH₃ | H | CH₃ | |
| SCH₂CH(CH₂)(CH₂) (cyclopropyl) | H | CH₃ | |
| SOCH₂CH(CH₂)(CH₂) (cyclopropyl) | H | CH₃ | |
| SO₂CH₂CH(CH₂)(CH₂) (cyclopropyl) | H | CH₃ | |
| SCH₃ | H | OCH₃ | |
| SOCH₃ | H | OCH₃ | |
| SO₂CH₃ | H | OCH₃ | |
| SC₂H₅ | H | OCH₃ | |
| SOC₂H₅ | H | OCH₃ | |
| SO₂C₂H₅ | H | OCH₃ | 175–180° |
| S(CH₂)₂CH₃ | H | OCH₃ | |
| SO(CH₂)₂CH₃ | H | OCH₃ | |
| SO₂(CH₂)₂CH₃ | H | OCH₃ | |
| SCH(CH₃)₂ | H | OCH₃ | |
| SOCH(CH₃)₂ | H | OCH₃ | |
| SO₂CH(CH₃)₂ | H | OCH₃ | |
| S(CH₂)₃CH₃ | H | OCH₃ | |
| SO(CH₂)₃CH₃ | H | OCH₃ | |
| SO₂(CH₂)₃CH₃ | H | OCH₃ | |
| SCH₂CH(CH₃)₂ | H | OCH₃ | |
| SOCH₂CH(CH₃)₂ | H | OCH₃ | |
| SO₂CH₂CH(CH₃)₂ | H | OCH₃ | |
| SCH(CH₃)CH₂CH₃ | H | OCH₃ | |
| SOCH(CH₃)CH₂CH₃ | H | OCH₃ | |
| SO₂CH(CH₃)CH₂CH₃ | H | OCH₃ | |
| SC(CH₃)₃ | H | OCH₃ | |
| SOC(CH₃)₃ | H | OCH₃ | |
| SO₂C(CH₃)₃ | H | OCH₃ | |
| SCH₂CH=CH₂ | H | OCH₃ | |
| SOCH₂CH=CH₂ | H | OCH₃ | |
| SO₂CH₂CH=CH₂ | H | OCH₃ | |
| SCH₂CH=CHCH₃ | H | OCH₃ | |
| SOCH₂CH=CHCH₃ | H | OCH₃ | |
| SO₂CH₂CH=CHCH₃ | H | OCH₃ | |
| SCH₂CH(CH₂)(CH₂) (cyclopropyl) | H | OCH₃ | |
| SOCH₂CH(CH₂)(CH₂) (cyclopropyl) | H | OCH₃ | |
| SO₂CH₂CH(CH₂)(CH₂) (cyclopropyl) | H | OCH₃ | |
| S(CH₂)₃CH₃ | H | C₂H₅ | |
| SO(CH₂)₃CH₃ | H | C₂H₅ | |
| SO₂(CH₂)₃CH₃ | H | C₂H₅ | |
| SCH₂CH(CH₃)₂ | H | C₂H₅ | |
| SOCH₂CH(CH₃)₂ | H | C₂H₅ | |
| SO₂CH₂CH(CH₃)₂ | H | C₂H₅ | |
| SCH(CH₃)CH₂CH₃ | H | C₂H₅ | |
| SOCH(CH₃)CH₂CH₃ | H | C₂H₅ | |
| SO₂CH(CH₃)CH₂CH₃ | H | C₂H₅ | |
| SC(CH₃)₃ | H | C₂H₅ | |
| SOC(CH₃)₃ | H | C₂H₅ | |
| SO₂C(CH₃)₃ | H | C₂H₅ | |
| SCH₂CH=CH₂ | H | C₂H₅ | |
| SOCH₂CH=CH₂ | H | C₂H₅ | |
| SO₂CH₂CH=CH₂ | H | C₂H₅ | |
| SCH₂CH=CHCH₃ | H | C₂H₅ | |
| SOCH₂CH=CHCH₃ | H | C₂H₅ | |
| SO₂CH₂CH=CHCH₃ | H | C₂H₅ | |
| SCH₂CH(CH₂)(CH₂) (cyclopropyl) | H | C₂H₅ | |
| SOCH₂CH(CH₂)(CH₂) (cyclopropyl) | H | C₂H₅ | |
| SO₂CH₂CH(CH₂)(CH₂) (cyclopropyl) | H | C₂H₅ | |
| SCH₃ | H | OC₂H₅ | |
| SOCH₃ | H | OC₂H₅ | |
| SO₂CH₃ | H | OC₂H₅ | |
| SC₂H₅ | H | OC₂H₅ | |
| SOC₂H₅ | H | OC₂H₅ | |
| SO₂C₂H₅ | H | OC₂H₅ | |
| S(CH₂)₂CH₃ | H | OC₂H₅ | |
| SO(CH₂)₂CH₃ | H | OC₂H₅ | |
| SO₂(CH₂)₂CH₃ | H | OC₂H₅ | |
| SCH(CH₃)₂ | H | OC₂H₅ | |
| SOCH(CH₃)₂ | H | OC₂H₅ | |
| SO₂CH(CH₃)₂ | H | OC₂H₅ | |
| S(CH₂)₃CH₃ | H | OC₂H₅ | |
| SO(CH₂)₃CH₃ | H | OC₂H₅ | |
| SO₂(CH₂)₃CH₃ | H | OC₂H₅ | |
| SCH₂CH(CH₃)₂ | H | OC₂H₅ | |
| SOCH₂CH(CH₃)₂ | H | OC₂H₅ | |
| SO₂CH₂CH(CH₃)₂ | H | OC₂H₅ | |
| SCH(CH₃)CH₂CH₃ | H | OC₂H₅ | |
| SOCH(CH₃)CH₂CH₃ | H | OC₂H₅ | |
| SO₂CH(CH₃)CH₂CH₃ | H | OC₂H₅ | |

TABLE VI-continued

Structure: Benzene ring with H, R1, R2 substituents, connected via SO2NHCNH (with C=O) to pyrimidine ring with X and NH2 substituents.

| R₁ | R₂ | X | m.p. (°C.) |
|---|---|---|---|
| SC(CH₃)₃ | H | OC₂H₅ | |
| SOC(CH₃)₃ | H | OC₂H₅ | |
| SO₂C(CH₃)₃ | H | OC₂H₅ | |
| SCH₂CH=CH₂ | H | OC₂H₅ | |
| SOCH₂CH=CH₂ | H | OC₂H₅ | |
| SO₂CH₂CH=CH₂ | H | OC₂H₅ | |
| SCH₂CH=CHCH₃ | H | OC₂H₅ | |
| SOCH₂CH=CHCH₃ | H | OC₂H₅ | |
| SO₂CH₂CH=CHCH₃ | H | OC₂H₅ | |
| SCH₂CH(cyclopropyl) | H | OC₂H₅ | |
| SOCH₂CH(cyclopropyl) | H | OC₂H₅ | |
| SO₂CH₂CH(cyclopropyl) | H | OC₂H₅ | |
| S(CH₂)₃CH₃ | H | CH₂OCH₃ | |
| SO(CH₂)₃CH₃ | H | CH₂OCH₃ | |
| SO₂(CH₂)₃CH₃ | H | CH₂OCH₃ | |
| SCH₂CH(CH₃)₂ | H | CH₂OCH₃ | |
| SOCH₂CH(CH₃)₂ | H | CH₂OCH₃ | |
| SO₂CH₂CH(CH₃)₂ | H | CH₂OCH₃ | |
| SCH(CH₃)CH₂CH₃ | H | CH₂OCH₃ | |
| SOCH(CH₃)CH₂CH₃ | H | CH₂OCH₃ | |
| SO₂CH(CH₃)CH₂CH₃ | H | CH₂OCH₃ | |
| SC(CH₃)₃ | H | CH₂OCH₃ | |
| SOC(CH₃)₃ | H | CH₂OCH₃ | |
| SO₂C(CH₃)₃ | H | CH₂OCH₃ | |
| SCH₂CH=CH₂ | H | CH₂OCH₃ | |
| SOCH₂CH=CH₂ | H | CH₂OCH₃ | |
| SO₂CH₂CH=CH₂ | H | CH₂OCH₃ | |
| SCH₂CH=CHCH₃ | H | CH₂OCH₃ | |
| SOCH₂CH=CHCH₃ | H | CH₂OCH₃ | |
| SO₂CH₂CH=CHCH₃ | H | CH₂OCH₃ | |
| SCH₂CH(cyclopropyl) | H | CH₂OCH₃ | |
| SOCH₂CH(cyclopropyl) | H | CH₂OCH₃ | |
| SO₂CH₂CH(cyclopropyl) | H | CH₂OCH₃ | |
| SO₂CH₃ | 3-CH₃ | CH₃ | |
| SO₂CH₃ | 5-CF₃ | CH₃ | |
| SO₂CH₃ | 5-Cl | OCH₃ | |
| SO₂CH₃ | 5-OCH₃ | OCH₃ | |
| SO₂CH₃ | 5-NO₂ | OC₂H₅ | |
| SO₂CH₃ | 6-CH₃ | OCH₃ | |
| SC₂H₅ | 5-CH₃ | CH₃ | |
| SOC₂H₅ | 5-CF₃ | OCH₃ | |
| SO₂C₂H₅ | 5-Cl | OCH₃ | |
| SO₂C₂H₅ | 6-Br | OC₂H₅ | |
| SO₂(CH₂)₂CH₃ | 3-CH₃ | CH₃ | |
| SO₂(CH₂)₂CH₃ | 3-Br | OCH₃ | |
| SO₂(CH₂)₂CH₃ | 5-CH₃ | OC₂H₅ | |
| SO₂(CH₂)₂CH₃ | 5-CF₃ | OCH₃ | |
| SO₂(CH₂)₂CH₃ | 5-OCH₃ | CH₃ | |
| SO₂(CH₂)₂CH₃ | 5-Cl | OCH₃ | |
| SO₂(CH₂)₂CH₃ | 6-NO₂ | CH₃ | |
| SO₂(CH₂)₂CH₃ | 6-CH₃ | OCH₃ | |
| S(CH₂)₃CH₃ | 5-CH₃ | OC₂H₅ | |
| SO(CH₂)₃CH₃ | 5-CF₃ | OCH₃ | |
| SO₂CH₂CH=CH₂ | 3-Br | CH₃ | |
| SO₂CH₂CH=CH₂ | 3-Cl | OCH₃ | |
| SO₂CH₂CH=CH₂ | 5-CH₃ | OC₂H₅ | |
| SO₂CH₂CH=CH₂ | 5-OCH₃ | C₂H₅ | |
| SO₂CH₂CH=CH₂ | 5-CF₃ | C₂H₅ | |
| SO₂CH₂CH=CH₂ | 6-NO₂ | CH₂OCH₃ | |
| SCH₂C(CH₃)=CH₂ | 5-CF₃ | OCH₃ | |
| SOCH₂CH(cyclopropyl) | 3-CH₃ | OC₂H₅ | |
| SO₂CH₂CH(cyclopropyl) | 5-Cl | CH₂OCH₃ | |

TABLE VII

Structure: Benzene ring with H, R1, R2 substituents, connected via SO2NHCNH (with C=O) to pyrimidine ring with X and NHCH3 substituents.

| R₁ | R₂ | X | m.p. (°C.) |
|---|---|---|---|
| SCH₃ | H | CH₃ | |
| SOCH₃ | H | CH₃ | |
| SO₂CH₃ | H | CH₃ | |
| SC₂H₅ | H | CH₃ | |
| SOC₂H₅ | H | CH₃ | |
| SO₂C₂H₅ | H | CH₃ | |
| S(CH₂)₂CH₃ | H | CH₃ | |
| SO(CH₂)₂CH₃ | H | CH₃ | |
| SO₂(CH₂)₂CH₃ | H | CH₃ | |
| SCH(CH₃)₂ | H | CH₃ | |
| SOCH(CH₃)₂ | H | CH₃ | |
| SO₂CH(CH₃)₂ | H | CH₃ | |
| S(CH₂)₃CH₃ | H | CH₃ | |
| SO(CH₂)₃CH₃ | H | CH₃ | |
| SO₂(CH₂)₃CH₃ | H | CH₃ | |
| SCH₂CH(CH₃)₂ | H | CH₃ | |
| SOCH₂CH(CH₃)₂ | H | CH₃ | |
| SO₂CH₂CH(CH₃)₂ | H | CH₃ | |
| SCH(CH₃)CH₂CH₃ | H | CH₃ | |
| SOCH(CH₃)CH₂CH₃ | H | CH₃ | |
| SO₂CH(CH₃)CH₂CH₃ | H | CH₃ | |
| SC(CH₃)₃ | H | CH₃ | |
| SOC(CH₃)₃ | H | CH₃ | |
| SO₂C(CH₃)₃ | H | CH₃ | |
| SCH₂CH=CH₂ | H | CH₃ | |
| SOCH₂CH=CH₂ | H | CH₃ | |
| SO₂CH₂CH=CH₂ | H | CH₃ | |
| SCH₂CH=CHCH₃ | H | CH₃ | |
| SOCH₂CH=CHCH₃ | H | CH₃ | |
| SO₂CH₂CH=CHCH₃ | H | CH₃ | |

TABLE VII-continued

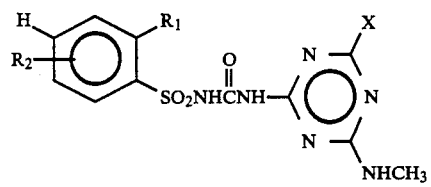

| R₁ | R₂ | X | m.p. (°C.) |
|---|---|---|---|
| SCH₂CH(CH₂)(CH₂) | H | CH₃ | |
| SOCH₂CH(CH₂)(CH₂) | H | CH₃ | |
| SO₂CH₂CH(CH₂)(CH₂) | H | CH₃ | |
| SCH₃ | H | OCH₃ | |
| SOCH₃ | H | OCH₃ | |
| SO₂CH₃ | H | OCH₃ | 205–240° |
| SC₂H₅ | H | OCH₃ | |
| SOC₂H₅ | H | OCH₃ | |
| SO₂C₂H₅ | H | OCH₃ | |
| S(CH₂)₂CH₃ | H | OCH₃ | |
| SO(CH₂)₂CH₃ | H | OCH₃ | |
| SO₂(CH₂)₂CH₃ | H | OCH₃ | |
| SCH(CH₃)₂ | H | OCH₃ | |
| SOCH(CH₃)₂ | H | OCH₃ | |
| SO₂CH(CH₃)₂ | H | OCH₃ | |
| S(CH₂)₃CH₃ | H | OCH₃ | |
| SO(CH₂)₃CH₃ | H | OCH₃ | |
| SO₂(CH₂)₃CH₃ | H | OCH₃ | |
| SCH₂CH(CH₃)₂ | H | OCH₃ | |
| SOCH₂CH(CH₃)₂ | H | OCH₃ | |
| SO₂CH₂CH(CH₃)₂ | H | OCH₃ | |
| SCH(CH₃)CH₂CH₃ | H | OCH₃ | |
| SOCH(CH₃)CH₂CH₃ | H | OCH₃ | |
| SO₂CH(CH₃)CH₂CH₃ | H | OCH₃ | |
| SC(CH₃)₃ | H | OCH₃ | |
| SOC(CH₃)₃ | H | OCH₃ | |
| SO₂C(CH₃)₃ | H | OCH₃ | |
| SCH₂CH=CH₂ | H | OCH₃ | |
| SOCH₂CH=CH₂ | H | OCH₃ | |
| SO₂CH₂CH=CH₂ | H | OCH₃ | |
| SCH₂CH=CHCH₃ | H | OCH₃ | |
| SOCH₂CH=CHCH₃ | H | OCH₃ | |
| SO₂CH₂CH=CHCH₃ | H | OCH₃ | |
| SCH₂CH(CH₂)(CH₂) | H | OCH₃ | |
| SOCH₂CH(CH₂)(CH₂) | H | OCH₃ | |
| SO₂CH₂CH(CH₂)(CH₂) | H | OCH₃ | |
| S(CH₂)₃CH₃ | H | C₂H₅ | |
| SO(CH₂)₃CH₃ | H | C₂H₅ | |
| SO₂(CH₂)₃CH₃ | H | C₂H₅ | |
| SCH₂CH(CH₃)₂ | H | C₂H₅ | |
| SOCH₂CH(CH₃)₂ | H | C₂H₅ | |
| SO₂CH₂CH(CH₃)₂ | H | C₂H₅ | |
| SCH(CH₃)CH₂CH₃ | H | C₂H₅ | |
| SOCH(CH₃)CH₂CH₃ | H | C₂H₅ | |
| SO₂CH(CH₃)CH₂CH₃ | H | C₂H₅ | |
| SC(CH₃)₃ | H | C₂H₅ | |
| SOC(CH₃)₃ | H | C₂H₅ | |

TABLE VII-continued

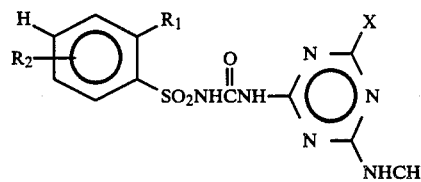

| R₁ | R₂ | X | m.p. (°C.) |
|---|---|---|---|
| SO₂C(CH₃)₃ | H | C₂H₅ | |
| SCH₂CH=CH₂ | H | C₂H₅ | |
| SOCH₂CH=CH₂ | H | C₂H₅ | |
| SO₂CH₂CH=CH₂ | H | C₂H₅ | |
| SCH₂CH=CHCH₃ | H | C₂H₅ | |
| SOCH₂CH=CHCH₃ | H | C₂H₅ | |
| SO₂CH₂CH=CHCH₃ | H | C₂H₅ | |
| SCH₂CH(CH₂)(CH₂) | H | C₂H₅ | |
| SOCH₂CH(CH₂)(CH₂) | H | C₂H₅ | |
| SO₂CH₂CH(CH₂)(CH₂) | H | C₂H₅ | |
| SCH₃ | H | OC₂H₅ | |
| SOCH₃ | H | OC₂H₅ | |
| SO₂CH₃ | H | OC₂H₅ | 210–214° |
| SC₂H₅ | H | OC₂H₅ | |
| SOC₂H₅ | H | OC₂H₅ | |
| SO₂C₂H₅ | H | OC₂H₅ | 163–167° |
| S(CH₂)₂CH₃ | H | OC₂H₅ | |
| SO(CH₂)₂CH₃ | H | OC₂H₅ | |
| SO₂(CH₂)₂CH₃ | H | OC₂H₅ | 168–171° |
| SCH(CH₃)₂ | H | OC₂H₅ | |
| SOCH(CH₃)₂ | H | OC₂H₅ | |
| SO₂CH(CH₃)₂ | H | OC₂H₅ | |
| S(CH₂)₃CH₃ | H | OC₂H₅ | |
| SO(CH₂)₃CH₃ | H | OC₂H₅ | |
| SO₂(CH₂)₃CH₃ | H | OC₂H₅ | |
| SCH₂CH(CH₃)₂ | H | OC₂H₅ | |
| SOCH₂CH(CH₃)₂ | H | OC₂H₅ | |
| SO₂CH₂CH(CH₃)₂ | H | OC₂H₅ | |
| SCH(CH₃)CH₂CH₃ | H | OC₂H₅ | |
| SOCH(CH₃)CH₂CH₃ | H | OC₂H₅ | |
| SO₂CH(CH₃)CH₂CH₃ | H | OC₂H₅ | |
| SC(CH₃)₃ | H | OC₂H₅ | |
| SOC(CH₃)₃ | H | OC₂H₅ | |
| SO₂C(CH₃)₃ | H | OC₂H₅ | |
| SCH₂CH=CH₂ | H | OC₂H₅ | |
| SOCH₂CH=CH₂ | H | OC₂H₅ | |
| SO₂CH₂CH=CH₂ | H | OC₂H₅ | |
| SCH₂CH=CHCH₃ | H | OC₂H₅ | |
| SOCH₂CH=CHCH₃ | H | OC₂H₅ | |
| SO₂CH₂CH=CHCH₃ | H | OC₂H₅ | |
| SCH₂CH(CH₂)(CH₂) | H | OC₂H₅ | |
| SOCH₂CH(CH₂)(CH₂) | H | OC₂H₅ | |
| SO₂CH₂CH(CH₂)(CH₂) | H | OC₂H₅ | |
| S(CH₂)₃CH₃ | H | CH₂OCH₃ | |
| SO(CH₂)₃CH₃ | H | CH₂OCH₃ | |
| SO₂(CH₂)₃CH₃ | H | CH₂OCH₃ | |

TABLE VII-continued

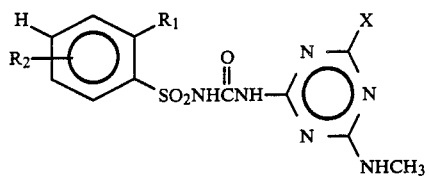

| R₁ | R₂ | X | m.p. (°C.) |
|---|---|---|---|
| SCH₂CH(CH₃)₂ | H | CH₂OCH₃ | |
| SOCH₂CH(CH₃)₂ | H | CH₂OCH₃ | |
| SO₂CH₂CH(CH₃)₂ | H | CH₂OCH₃ | |
| SCH(CH₃)CH₂CH₃ | H | CH₂OCH₃ | |
| SOCH(CH₃)CH₂CH₃ | H | CH₂OCH₃ | |
| SO₂CH(CH₃)CH₂CH₃ | H | CH₂OCH₃ | |
| SC(CH₃)₃ | H | CH₂OCH₃ | |
| SOC(CH₃)₃ | H | CH₂OCH₃ | |
| SO₂C(CH₃)₃ | H | CH₂OCH₃ | |
| SCH₂CH=CH₂ | H | CH₂OCH₃ | |
| SOCH₂CH=CH₂ | H | CH₂OCH₃ | |
| SO₂CH₂CH=CH₂ | H | CH₂OCH₃ | |
| SCH₂CH=CHCH₃ | H | CH₂OCH₃ | |
| SOCH₂CH=CHCH₃ | H | CH₂OCH₃ | |
| SO₂CH₂CH=CHCH₃ | H | CH₂OCH₃ | |
| SCH₂CH(-CH₂-CH₂-) (cyclopropyl) | H | CH₂OCH₃ | |
| SOCH₂CH(-CH₂-CH₂-) (cyclopropyl) | H | CH₂OCH₃ | |
| SO₂CH₂CH(-CH₂-CH₂-) (cyclopropyl) | H | CH₂OCH₃ | |
| SO₂CH₃ | 3-CH₃ | CH₃ | |
| SO₂CH₃ | 5-CF₃ | CH₃ | |
| SO₂CH₃ | 5-Cl | OCH₃ | |
| SO₂CH₃ | 5-OCH₃ | OCH₃ | |
| SO₂CH₃ | 5-NO₂ | OC₂H₅ | |
| SO₂CH₃ | 6-CH₃ | OCH₃ | |
| SC₂H₅ | 5-CH₃ | CH₃ | |
| SOC₂H₅ | 5-CF₃ | OCH₃ | |
| SO₂C₂H₅ | 5-Cl | OCH₃ | |
| SO₂C₂H₅ | 6-Br | OC₂H₅ | |
| SO₂(CH₂)₂CH₃ | 3-CH₃ | CH₃ | |
| SO₂(CH₂)₂CH₃ | 3-Br | OCH₃ | |
| SO₂(CH₂)₂CH₃ | 5-CH₃ | OCH₃ | |
| SO₂(CH₂)₂CH₃ | 5-CF₃ | OC₂H₅ | |
| SO₂(CH₂)₂CH₃ | 5-OCH₃ | CH₃ | |
| SO₂(CH₂)₂CH₃ | 5-Cl | OCH₃ | |
| SO₂(CH₂)₂CH₃ | 6-NO₂ | CH₃ | |
| SO₂(CH₂)₂CH₃ | 6-CH₃ | OCH₃ | |
| S(CH₂)₃CH₃ | 5-CH₃ | OC₂H₅ | |
| SO(CH₂)₃CH₃ | 5-CF₃ | OCH₃ | |
| SO₂CH₂CH=CH₂ | 3-Br | CH₃ | |
| SO₂CH₂CH=CH₂ | 3-Cl | OCH₃ | |
| SO₂CH₂CH=CH₂ | 5-CH₃ | OC₂H₅ | |
| SO₂CH₂CH=CH₂ | 5-OCH₃ | C₂H₅ | |
| SO₂CH₂CH=CH₂ | 5-CF₃ | C₂H₅ | |
| SO₂CH₂CH=CH₂ | 6-NO₂ | CH₂OCH₃ | |
| SCH₂C(CH₃)=CH₂ | 5-CF₃ | OCH₃ | |
| SOCH₂CH(-CH₂-CH₂-) (cyclopropyl) | 3-CH₃ | OC₂H₅ | |
| SO₂CH₂CH(-CH₂-CH₂-) (cyclopropyl) | 5-Cl | CH₂OCH₃ | |

TABLE VIII

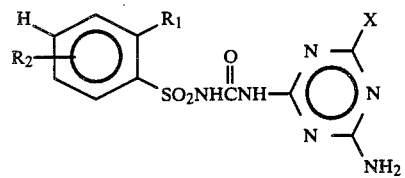

| R₁ | R₂ | X | m.p. (°C.) |
|---|---|---|---|
| SCH₃ | H | CH₃ | |
| SOCH₃ | H | CH₃ | |
| SO₂CH₃ | H | CH₃ | |
| SC₂H₅ | H | CH₃ | |
| SOC₂H₅ | H | CH₃ | |
| SO₂C₂H₅ | H | CH₃ | |
| S(CH₂)₂CH₃ | H | CH₃ | |
| SO(CH₂)₂CH₃ | H | CH₃ | |
| SO₂(CH₂)₂CH₃ | H | CH₃ | |
| SCH(CH₃)₂ | H | CH₃ | |
| SOCH(CH₃)₂ | H | CH₃ | |
| SO₂CH(CH₃)₂ | H | CH₃ | |
| S(CH₂)₃CH₃ | H | CH₃ | |
| SO(CH₂)₃CH₃ | H | CH₃ | |
| SO₂(CH₂)₃CH₃ | H | CH₃ | |
| SCH₂CH(CH₃)₂ | H | CH₃ | |
| SOCH₂CH(CH₃)₂ | H | CH₃ | |
| SO₂CH₂CH(CH₃)₂ | H | CH₃ | |
| SCH(CH₃)CH₂CH₃ | H | CH₃ | |
| SOCH(CH₃)CH₂CH₃ | H | CH₃ | |
| SO₂CH(CH₃)CH₂CH₃ | H | CH₃ | |
| SC(CH₃)₃ | H | CH₃ | |
| SOC(CH₃)₃ | H | CH₃ | |
| SO₂C(CH₃)₃ | H | CH₃ | |
| SCH₂CH=CH₂ | H | CH₃ | |
| SOCH₂CH=CH₂ | H | CH₃ | |
| SO₂CH₂CH=CH₂ | H | CH₃ | |
| SCH₂CH=CHCH₃ | H | CH₃ | |
| SOCH₂CH=CHCH₃ | H | CH₃ | |
| SO₂CH₂CH=CHCH₃ | H | CH₃ | |
| SCH₂CH(-CH₂-CH₂-) (cyclopropyl) | H | CH₃ | |
| SOCH₂CH(-CH₂-CH₂-) (cyclopropyl) | H | CH₃ | |
| SO₂CH₂CH(-CH₂-CH₂-) (cyclopropyl) | H | CH₃ | |
| SCH₃ | H | OCH₃ | |
| SOCH₃ | H | OCH₃ | |
| SO₂CH₃ | H | OCH₃ | >255° |
| SC₂H₅ | H | OCH₃ | |
| SOC₂H₅ | H | OCH₃ | |
| SO₂C₂H₅ | H | OCH₃ | >270° |
| S(CH₂)₂CH₃ | H | OCH₃ | |
| SO(CH₂)₂CH₃ | H | OCH₃ | |
| SO₂(CH₂)₂CH₃ | H | OCH₃ | |
| SCH(CH₃)₂ | H | OCH₃ | |
| SOCH(CH₃)₂ | H | OCH₃ | |
| SO₂CH(CH₃)₂ | H | OCH₃ | |
| S(CH₂)₃CH₃ | H | OCH₃ | |
| SO(CH₂)₃CH₃ | H | OCH₃ | |
| SO₂(CH₂)₃CH₃ | H | OCH₃ | |
| SCH₂CH(CH₃)₂ | H | OCH₃ | |
| SOCH₂CH(CH₃)₂ | H | OCH₃ | |
| SO₂CH₂CH(CH₃)₂ | H | OCH₃ | |
| SCH(CH₃)CH₂CH₃ | H | OCH₃ | |
| SOCH(CH₃)CH₂CH₃ | H | OCH₃ | |
| SO₂CH(CH₃)CH₂CH₃ | H | OCH₃ | |
| SC(CH₃)₃ | H | OCH₃ | |
| SOC(CH₃)₃ | H | OCH₃ | |
| SO₂C(CH₃)₃ | H | OCH₃ | |
| SCH₂CH=CH₂ | H | OCH₃ | |

TABLE VIII-continued structure: phenyl with H, R1, R2 substituents, -SO2NHC(O)NH- linked to pyrimidine with X and NH2

| R₁ | R₂ | X | m.p. (°C.) |
|---|---|---|---|
| SOCH₂CH=CH₂ | H | OCH₃ | |
| SO₂CH₂CH=CH₂ | H | OCH₃ | |
| SCH₂CH=CHCH₃ | H | OCH₃ | |
| SOCH₂CH=CHCH₃ | H | OCH₃ | |
| SO₂CH₂CH=CHCH₃ | H | OCH₃ | |
| SCH₂CH(cyclopropyl) | H | OCH₃ | |
| SOCH₂CH(cyclopropyl) | H | OCH₃ | |
| SO₂CH₂CH(cyclopropyl) | H | OCH₃ | |
| S(CH₂)₃CH₃ | H | C₂H₅ | |
| SO(CH₂)₃CH₃ | H | C₂H₅ | |
| SO₂(CH₂)₃CH₃ | H | C₂H₅ | |
| SCH₂CH(CH₃)₂ | H | C₂H₅ | |
| SOCH₂CH(CH₃)₂ | H | C₂H₅ | |
| SO₂CH₂CH(CH₃)₂ | H | C₂H₅ | |
| SCH(CH₃)CH₂CH₃ | H | C₂H₅ | |
| SOCH(CH₃)CH₂CH₃ | H | C₂H₅ | |
| SO₂CH(CH₃)CH₂CH₃ | H | C₂H₅ | |
| SC(CH₃)₃ | H | C₂H₅ | |
| SOC(CH₃)₃ | H | C₂H₅ | |
| SO₂C(CH₃)₃ | H | C₂H₅ | |
| SCH₂CH=CH₂ | H | C₂H₅ | |
| SOCH₂CH=CH₂ | H | C₂H₅ | |
| SO₂CH₂CH=CH₂ | H | C₂H₅ | |
| SCH₂CH=CHCH₃ | H | C₂H₅ | |
| SOCH₂CH=CHCH₃ | H | C₂H₅ | |
| SO₂CH₂CH=CHCH₃ | H | C₂H₅ | |
| SCH₂CH(cyclopropyl) | H | OC₂H₅ | |
| SOCH₂CH(cyclopropyl) | H | OC₂H₅ | |
| SO₂CH₂CH(cyclopropyl) | H | OC₂H₅ | |
| SCH₃ | H | OC₂H₅ | |
| SOCH₃ | H | OC₂H₅ | |
| SO₂CH₃ | H | OC₂H₅ | |
| SC₂H₅ | H | OC₂H₅ | |
| SOC₂H₅ | H | OC₂H₅ | |
| SO₂C₂H₅ | H | OC₂H₅ | >270° |
| S(CH₂)₂CH₃ | H | OC₂H₅ | |
| SO(CH₂)₂CH₃ | H | OC₂H₅ | |
| SO₂(CH₂)₂CH₃ | H | OC₂H₅ | |
| SCH(CH₃)₂ | H | OC₂H₅ | |
| SOCH(CH₃)₂ | H | OC₂H₅ | |
| SO₂CH(CH₃)₂ | H | OC₂H₅ | |
| S(CH₂)₃CH₃ | H | OC₂H₅ | |
| SO(CH₂)₃CH₃ | H | OC₂H₅ | |
| SO₂(CH₂)₃CH₃ | H | OC₂H₅ | |
| SCH₂CH(CH₃)₂ | H | OC₂H₅ | |
| SOCH₂CH(CH₃)₂ | H | OC₂H₅ | |
| SO₂CH₂CH(CH₃)₂ | H | OC₂H₅ | |
| SCH(CH₃)CH₂CH₃ | H | OC₂H₅ | |
| SOCH(CH₃)CH₂CH₃ | H | OC₂H₅ | |
| SO₂CH(CH₃)CH₂CH₃ | H | OC₂H₅ | |
| SC(CH₃)₃ | H | OC₂H₅ | |
| SOC(CH₃)₃ | H | OC₂H₅ | |
| SO₂C(CH₃)₃ | H | OC₂H₅ | |
| SCH₂CH=CH₂ | H | OC₂H₅ | |
| SOCH₂CH=CH₂ | H | OC₂H₅ | |
| SO₂CH₂CH=CH₂ | H | OC₂H₅ | |
| SCH₂CH=CHCH₃ | H | OC₂H₅ | |
| SOCH₂CH=CHCH₃ | H | OC₂H₅ | |
| SO₂CH₂CH=CHCH₃ | H | OC₂H₅ | |
| SCH₂CH(cyclopropyl) | H | OC₂H₅ | |
| SOCH₂CH(cyclopropyl) | H | OC₂H₅ | |
| SO₂CH₂CH(cyclopropyl) | H | OC₂H₅ | |
| S(CH₂)₃CH₃ | H | CH₂OCH₃ | |
| SO(CH₂)₃CH₃ | H | CH₂OCH₃ | |
| SO₂(CH₂)₃CH₃ | H | CH₂OCH₃ | |
| SCH₂CH(CH₃)₂ | H | CH₂OCH₃ | |
| SOCH₂CH(CH₃)₂ | H | CH₂OCH₃ | |
| SO₂CH₂CH(CH₃)₂ | H | CH₂OCH₃ | |
| SCH(CH₃)CH₂CH₃ | H | CH₂OCH₃ | |
| SOCH(CH₃)CH₂CH₃ | H | CH₂OCH₃ | |
| SO₂CH(CH₃)CH₂CH₃ | H | CH₂OCH₃ | |
| SC(CH₃)₃ | H | CH₂OCH₃ | |
| SOC(CH₃)₃ | H | CH₂OCH₃ | |
| SO₂C(CH₃)₃ | H | CH₂OCH₃ | |
| SCH₂CH=CH₂ | H | CH₂OCH₃ | |
| SOCH₂CH=CH₂ | H | CH₂OCH₃ | |
| SO₂CH₂CH=CH₂ | H | CH₂OCH₃ | |
| SCH₂CH=CHCH₃ | H | CH₂OCH₃ | |
| SOCH₂CH=CHCH₃ | H | CH₂OCH₃ | |
| SO₂CH₂CH=CHCH₃ | H | CH₂OCH₃ | |
| SCH₂CH(cyclopropyl) | H | CH₂OCH₃ | |
| SOCH₂CH(cyclopropyl) | H | CH₂OCH₃ | |
| SO₂CH₂CH(cyclopropyl) | H | CH₂OCH₃ | |
| SO₂CH₃ | 3-CH₃ | CH₃ | |
| SO₂CH₃ | 5-CF₃ | CH₃ | |
| SO₂CH₃ | 5-Cl | OCH₃ | |
| SO₂CH₃ | 5-OCH₃ | OCH₃ | |
| SO₂CH₃ | 5-NO₂ | OC₂H₅ | |
| SO₂CH₃ | 6-CH₃ | OCH₃ | |
| SC₂H₅ | 5-CH₃ | CH₃ | |
| SOC₂H₅ | 5-CF₃ | OCH₃ | |
| SO₂C₂H₅ | 5-Cl | OCH₃ | |

TABLE VIII-continued $$\text{H} \underset{R_2}{\overset{R_1}{\diagdown}} \!\!\! \bigcirc \!\!\! -SO_2NHCNH-\!\!\! \bigcirc \!\!\! \overset{N}{\underset{N}{\diagdown}}\!\!\! \overset{X}{\underset{NH_2}{\diagdown}}$$

| $R_1$ | $R_2$ | X | m.p. (°C.) |
|---|---|---|---|
| $SO_2C_2H_5$ | 6-Br | $OC_2H_5$ | |
| $SO_2(CH_2)_2CH_3$ | 3-$CH_3$ | $CH_3$ | |
| $SO_2(CH_2)_2CH_3$ | 3-Br | $OCH_3$ | |
| $SO_2(CH_2)_2CH_3$ | 5-$CH_3$ | $OCH_3$ | |
| $SO_2(CH_2)_2CH_3$ | 5-$CF_3$ | $OC_2H_5$ | |
| $SO_2(CH_2)_2CH_3$ | 5-$OCH_3$ | $CH_3$ | |
| $SO_2(CH_2)_2CH_3$ | 5-Cl | $OCH_3$ | |
| $SO_2(CH_2)_2CH_3$ | 6-$NO_2$ | $CH_3$ | |
| $SO_2(CH_2)_2CH_3$ | 6-$CH_3$ | $OCH_3$ | |
| $S(CH_2)_3CH_3$ | 5-$CH_3$ | $OC_2H_5$ | |
| $SO(CH_2)_3CH_3$ | 5-$CF_3$ | $OCH_3$ | |
| $SO_2CH_2CH=CH_2$ | 3-Br | $CH_3$ | |
| $SO_2CH_2CH=CH_2$ | 3-Cl | $OCH_3$ | |
| $SO_2CH_2CH=CH_2$ | 5-$CH_3$ | $OC_2H_5$ | |
| $SO_2CH_2CH=CH_2$ | 5-$OCH_3$ | $C_2H_5$ | |
| $SO_2CH_2CH=CH_2$ | 5-$CF_3$ | $C_2H_5$ | |
| $SO_2CH_2CH=CH_2$ | 6-$NO_2$ | $CH_2OCH_3$ | |
| $SCH_2C(CH_3)=CH_2$ | 5-$CF_3$ | $OCH_3$ | |
| $SOCH_2CH\overset{CH_2}{\underset{CH_2}{\diagdown}}$ | 3-$CH_3$ | $OC_2H_5$ | |
| $SO_2CH_2CH\overset{CH_2}{\underset{CH_2}{\diagdown}}$ | 5-Cl | $CH_2OCH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IX

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encylopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

Wettable Powder

| | |
|---|---|
| N—[(4-dimethylamino-6-methoxy-1,3,5-triazin-2-yl)-aminocarbonyl]-2-(methylsulfonyl)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 5

Wettable Powder

| | |
|---|---|
| N—[(4-chloro-6-ethoxypyrimidin-2-yl)aminocarbonyl]-2-(propylsulfonyl)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 6

Granule

| | |
|---|---|
| Wettable Powder of Example 5 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 7

Extruded Pellet

| | |
|---|---|
| N—[(4-dimethylamino-6-methoxy-1,3,5-triazin-2-yl)-aminocarbonyl]-2-(propylsulfonyl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

Oil Suspension

| | |
|---|---|
| N—[(4-dimethylamino-6-methoxy-1,3,5-triazin-2-yl)-aminocarbonyl]-2-(methylsulfonyl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

Wettable Powder

| | |
|---|---|
| N—[(4-chloro-6-ethoxypyrimidin-2-yl)aminocarbonyl]-2-(propylsulfonyl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

Low Strength Granule

| | |
|---|---|
| N—[(4-chloro-6-methoxypyrimidin-2-yl)aminocarbonyl]-2-(propylsulfonyl)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 11

Aqueous Suspension

| | |
|---|---|
| N—[(4-dimethylamino-6-methoxy-1,3,5-triazin-2-yl)-aminocarbonyl]-2-(propylsulfonyl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 12

Solution

| | |
|---|---|
| N—[(4-dimethylamino-6-methoxy-1,3,5-triazin-2-yl)-aminocarbonyl]-2-(methylsulfonyl)benzenesulfonamide | 5% |
| water | 95% |

The salt is added directly to the water with stirring to produce the solution, which may then be packaged for use.

EXAMPLE 13

Low Strength Granule

| | |
|---|---|
| N—[(4-chloro-6-ethoxypyrimidin-2-yl)aminocarbonyl]-2-(propylsulfonyl)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

Granule

| | |
|---|---|
| N—[(4-chloro-6-methoxypyrimidin-2-yl)aminocarbonyl]-2-(propylsulfonyl)benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 15

High Strength Concentrate

| | |
|---|---|
| N—[(4-dimethylamino-6-methoxy-1,3,5-triazin-2-yl)-aminocarbonyl]-2-(propylsulfonyl)benzenesulfonamide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 16

Wettable Powder

| | |
|---|---|
| N—[(4-dimethylamino-6-methoxy-1,3,5-triazin-2-yl)-aminocarbonyl]-2-(methylsulfonyl)benzenesulfonamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 17

Wettable Powder

| | |
|---|---|
| N—[(4-chloro-6-ethoxypyrimidin-2-yl)aminocarbonyl]-2-(propylsulfonyl)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Oil Suspension

| | |
|---|---|
| N—[(4-dimethylamino-6-methoxy-1,3,5-triazin-2-yl)-aminocarbonyl]-2-(propylsulfonyl)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

Dust

| | |
|---|---|
| N—[(4-chloro-6-methoxypyrimidin-2-yl)aminocarbonyl]-2-(propylsulfonyl)benzenesulfonamide | 10% |
| attapulgite | 10% |
| Pyrophyllite | 80% |

The active ingredient is blended with attapulgite and then passed through a hammer mill to produce particles substantially all below 200 microns. The ground concentrate is then blended with powdered pyrophyllite until homogeneous.

EXAMPLE 20

Emulsifiable Concentrate

| | |
|---|---|
| N—[(4-chloro-6-methoxypyrimidin-2-yl)aminocarbonyl]-2-(propylsulfonyl)benzenesulfonamide | 20% |
| chlorobenzene | 74% |
| sorbitan monostearate and polyoxyethylene condensates thereof | 6% |

The ingredients are combined and stirred to produce a solution which can be emulsified in water for application.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat, soybeans, cotton, corn and rape.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.02 to 5 kg/ha, the lower rates being suggested for use on lighter soils and/or those having a low organic matter content, for selective weed control or for situations where only short-term persistence is required.

The compounds of the invention may be used in combination with other commercial herbicides examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria spp.), barnyardgrass (*Echinochloa crusgalli*), wild oats (*Avena fatua*), sicklepod (*Cassia obtusifolia*), morningglory (Ipomoea spp.), cocklebur (*Xanthium pensylvanicum*), sorghum, corn, soybean, sugar beet, rice, wheat and purple nutsedge (*Cyperus rotundus*) tubers were planted and treated preemergence with the test chemicals dissolved in a nonphytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis,
E=emergence inhibition,
G=growth retardation,
H=formative effects,
U=unusual pigmentation,
X=axillary stimulation,
6Y=abscised buds or flowers.

The data indicate that the compounds tested are highly active herbicides. Certain compounds from within the scope have utility for selective weed control in soybeans, wheat, cotton, corn and rape.

Compounds

Compound No. 1

Compound No. 2

Compound No. 3

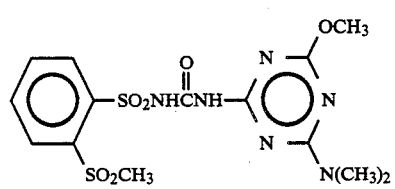
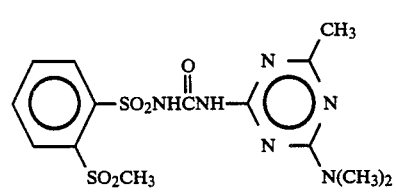
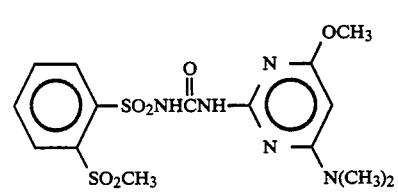

-continued
Compounds

Compound No. 4

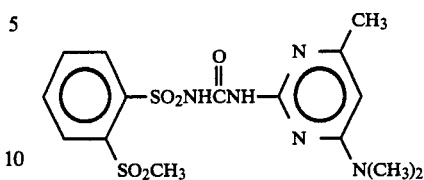

Compound No. 5

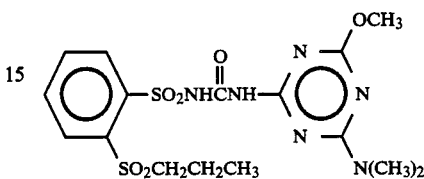

Compound No. 6

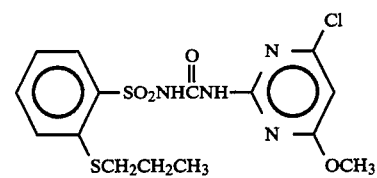

Compound No. 7

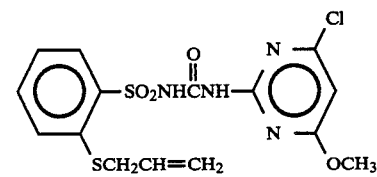

Compound No. 8

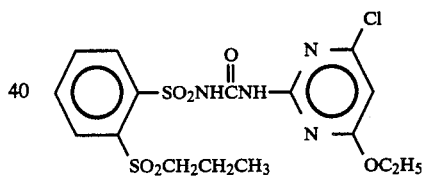

Compound No. 9

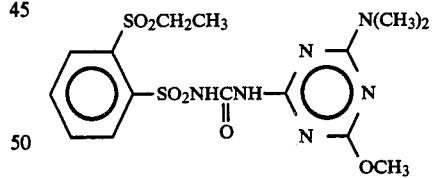

Compound No. 10

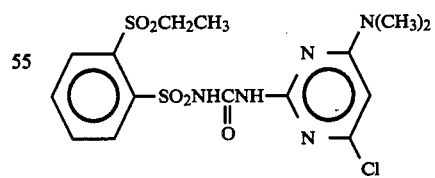

Compound No. 11

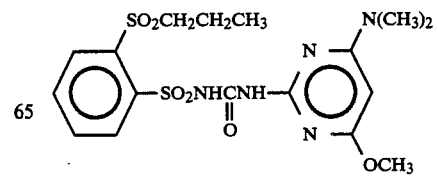

-continued
Compounds
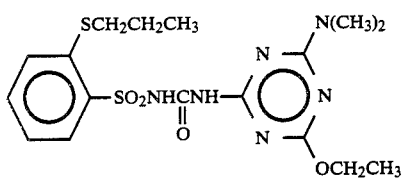
Compound No. 12
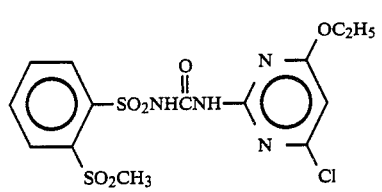
Compound No. 13
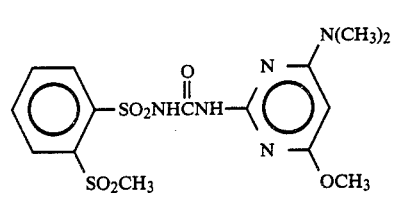
Compound No. 14
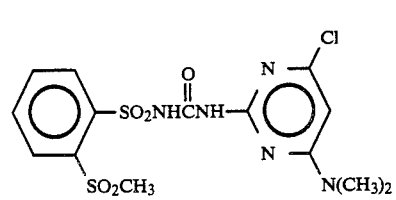
Compound No. 15
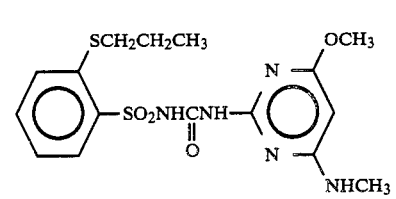
Compound No. 16
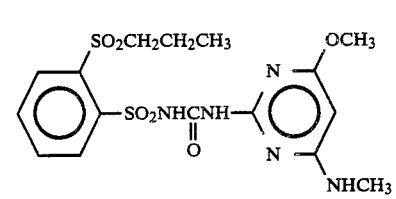
Compound No. 17
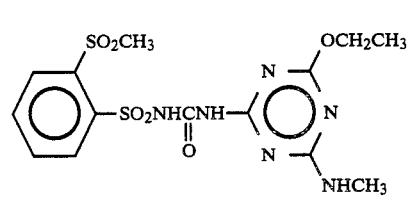
Compound No. 18
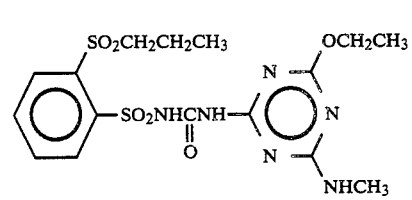
Compound No. 19
-continued
Compounds
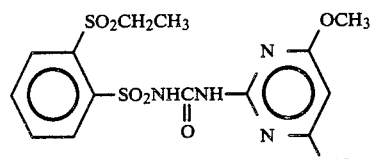
Compound No. 20
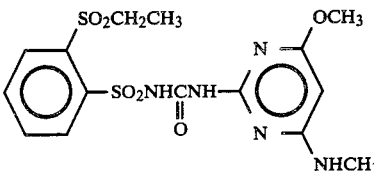
Compound No. 21
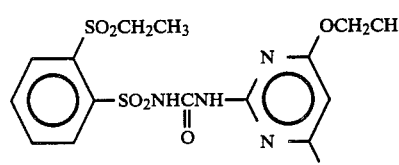
Compound No. 22
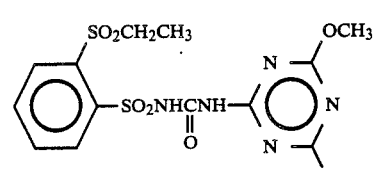
Compound No. 23
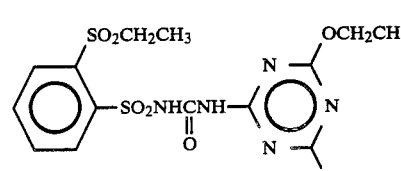
Compound No. 24
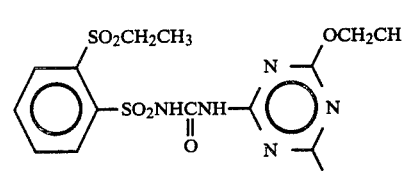
Compound No. 25
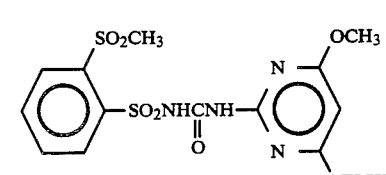
Compound No. 26
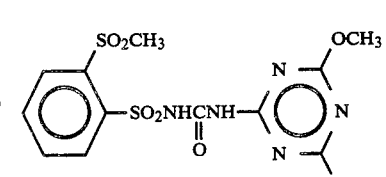
Compound No. 27
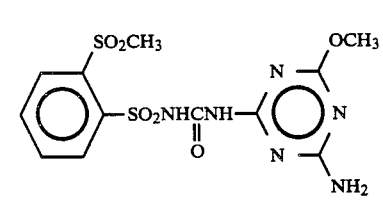
Compound No. 28

4,655,821

TABLE A

POST-EMERGENCE (kg/ha)

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 |
|---|---|---|---|---|---|---|---|---|---|---|---|
| | .4 | .05 | .05 | .05 | .05 | .05 | .05 | .05 | 50 | 50 | 50 |
| Bush bean | 9C | 3C,9G 6Y | 0 | 5C,9G,6Y | 5C,9G,6Y | 5C,9G,6Y | 2C,8G,6Y | 5C,9G,6Y | — | — | — |
| Cotton | 6C,9G | 2C,3H | 0 | 3C,5G | 3C,5H | 4C,9G | 2C,5G | 2C,5G | 4C,9G | 2C,9G | 2C |
| Morningglory | 4C,9G | 2C,8H | 0 | 3C,8G | 9C | 5C,9G | 0 | 5C,8G | 4C,8H | 1C,4G | 5C,6H |
| Cocklebur | 9C | 3G | 0 | 2C,6H | 9C | 4C,9H | 5H | 5G | 7G | 2C,6H | 4C,8H |
| Sicklepod | 9C | 3C | 0 | 2C,7H | 4C,9G | 3C,5G | 2C | 1C | 2C,3H | 3C,6G | 2C,2H |
| Nutsedge | 8G | 2C,5G | 0 | 2C | 2G | 3C,9G | 0 | 3G | 4G | 2C,6G | 0 |
| Crabgrass | 9C | 0 | 0 | 2C,9G | 1C,5G | 1C,3G | 2G | 0 | 2C,8G | 2C,7G | 2C,2G |
| Barnyardgrass | 9C | 1C,5G | 0 | 4C,9H | 2C,9H | 2C,6H | 2C,6H | 2C,6H | 2C,7G | 2C,9H | 3C,8H |
| Wild Oats | 9C | 2C,9H | 0 | 4C,8H | 2C,9G | 0 | 0 | 0 | 9H | 2C,8G | 8G |
| Corn | 9C | 2C | 0 | 3C,9G | 2C,9G | 3C,9G | 2C,6H | 2C,6H | 3C,9H | 5C,9G | 3G |
| Wheat | 7U,9C | 2C,8H | 0 | 2U,9H | 2U,9G | 2C,5G | 2C,5G | 1C,4G | 3U,9G | 4G | 3C,7H |
| Soybean | 9C | 2C,3H | 0 | 2C,8H,5X | 6C,9G | 1C,3G | 4G | 8G | 3C,8G | 3C,6G | 5G |
| Rice | 6C,9G | 3C,9G | 0 | 5C,9G | 6C,9G | 6G | 5G | 5G | 9G | 9G | 4C,9G |
| Sorghum | 5U,9G | 9G | 0 | 3C,9G | 2C,9G | 9G | 2C,7H | 2C,8H | 1U,9G | 3C,9G | 3C,9H |
| Sugar beet | — | — | — | — | 3C,8H | 3C,7G | 4G | 4G | 2C,4H | 10C | 2C,7G |

PRE-EMERGENCE

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 |
|---|---|---|---|---|---|---|---|---|---|---|---|
| Morningglory | 9G | 0 | 0 | 2C,8G | 9G | 8H | 2C,7H | 5C,9G | 8H | 8G | 2C,2H |
| Cocklebur | 9H | 0 | 0 | 2C,7G | 9H | 9H | 9H | 9H | 9H | 9H | 8G |
| Sicklepod | 2C,9G | 0 | 0 | 3C | 5G | 5G | 9G | 5G | 5G | 7H | — |
| Nutsedge | 2C,7G | 0 | 0 | 1C | 5G | 5G | 10E | 5G | 3G | 5G | 5G |
| Crabgrass | 7C,9G | 0 | 0 | 5C,9G | 1C | 1C | 2C | 1C | 4G | 6G | 0 |
| Barnyardgrass | 7C,9H | 2C | 0 | 3C,9H | 9H | 2C,5H | 4C,7H | 5G | 3C,7H | 4C,9H | 2C,6H |
| Wild Oats | 5C,9G | 1C,3G | 0 | 5C,9G | 2C,8G | 3G | 2C | 9G | 3C,8H | 4C,8G | 2C,6G |
| Corn | 4C,9G | 4G | 0 | 3C,9G | 9G | 3G | 0 | 3G | 2C,8G | 4C,9G | 2G |
| Soybean | 3C,9G | 2C,7G | 0 | 2C,9G | 2C,5G | 6G | 2C,5G | 6G | 5G | 2C,9G | 2C,6G |
| Rice | 8G | 2C,8G | 0 | 3C,3G | 0 | 0 | 0 | 0 | 2G | 1C,5G | 1H |
| Sorghum | 10E | — | 0 | 9H | 5C,9H | 2C,8H | 4C,7G | 10E | 3C,9G | 5C,9H | 2C,7G |
| Sugar beet | 6C,9H | — | — | 2C,9H | 2C,9H | 2C,9G | 2C,7H | 2C,7H | 3C,9G | 4C,9G | 2C,9G |
| Cotton | — | — | — | — | 10E | 3C,7G | 9G | 8G | 9C | 7G | 9H |
| | | | | | | | | | 9G | 8G | 1C |

(g/ha)

| | Cmpd. 12 | Cmpd. 13 | Cmpd. 14 | Compound 15 |
|---|---|---|---|---|
| | 50 | 50 | 50 | 50 | 400 |
| Bush bean | — | 3C,9G,6Y | 5C,9G,6Y | 2C,2H | 5C,9G,6Y |
| Cotton | 2C | 2C | 3C,5G | 4C,9G | 5C,9G |
| Morningglory | 5C,9H | 3C,5G | 3C,8G | 1C,5H | 3C,9G |
| Cocklebur | 4C,8H | 0 | 3C,6H | 2C | 3C,5G |
| Sicklepod | 2C,2H | 1C | 2C,7H | 2C | 2C,5G |
| Nutsedge | 0 | 3C,9G | 2C | 0 | 2C,4G |
| Crabgrass | 2C,2G | 2C,5G | 2C,9G | 5H | 0 |
| Barnyardgrass | 3C,8H | 5C,9H | 4C,9H | 5C,9H | 4C,8G |
| Wild Oats | 8G | 0 | 4C,8H | 4C,8H | 10C |
| Corn | 3G | 3C,8G | 3C,9G | 2C,8G | 9C |
| Soybean | 2C,7H | 1C,4G | 2U,9G | 2C,7H | 5C,9G |
| Rice | 2C,7H | 5G | 2C,8H,5X | 3H,7G | 5U,9H |
| Sorghum | 4C,9G | 3C,9G | 5C,9G | 5C,9G | 3H,9G |
| Sugar beet | 3C,9G | 3C,9G | 3C,9G | 3U,9G | 6C,9G |
| Cotton | 2G | 2G | — | — | 4U,9C |

POST-EMERGENCE (kg/ha)

| | Cmpd. 16 | Cmpd. 17 | Cmpd. 18 | Cmpd. 19 | Cmpd. 20 | Cmpd. 21 | Cmpd. 22 | Compound 23 | Compound 24 | Compound 25 | Compound 26 | Compound 27 | Compound 28 |
|---|---|---|---|---|---|---|---|---|---|---|---|---|---|
| | 0.05 | 0.05 | 0.05 | 0.05 | 0.05 | 0.05 | 0.05 | 0.4 | 0.05 | 0.4 | 0.4 | 0.4 | 0.05 |
| Bush bean | 3C,8H,6Y | 5C,6G,6Y | 1H | 2C,2H | — | — | — | — | — | — | — | — | — |
| Cotton | 2C,2G | 2C | 5C,8H | 2C,3H,7G | 0 | 4C,8G | 2G | 3C,3G | 3C,7G | 4C,8H | 3C,5G | 10C | 5G |
| Morningglory | 2C | 2C | 2C,8H | 3C,8H | 1C | 2C,3G | 2G | 3C,5H | 2C,5H | 4C,9G | 2C | 9C | 4C,6H |
| Cocklebur | 2C,8H | 5G | 2C,2H | 3C,8H | 1C | 3H | 7G | 1H | 1H | 3G | 2C,4G | 1C,3G | 3C |
| Sicklepod | 2C | 2C,5G | 2C,7H | 1H | 1C | 2C,4H | 2G | 1C,3G | 1C | 3C,6H | 2G | 4C,8G | 1C |
| Nutsedge | 0 | 0 | 2C | 3C,4H | 0 | 2C,7G | 0 | 0 | 2G | 5G | 0 | 2G | 3C,3H |
| Crabgrass | 4G | 2C,6G | 2C,7G | 2C,4G | 2H | 2C,8G | 2C,7G | 5G | 1C,3G | 3C,8H | 3C,8G | 3C,9G | 2C,5G |
| Barnyardgrass | 2C,5H | 3C,8H | 3C,9G | 2C,4H | 0 | 3C,9H | 4C,9H | 5G,2C | 0 | 5C,9H | 4C,9H | 5C,9H | 2C,3H |
| Wild Oats | 5C,9G | 2C | 2C,9H | 0 | 0 | 2C,8G | 2C,3G | 5C,7H | 3C,5G | 5C,9G | 9C | 3C,9G | 2C,7G |
| Corn | 3C,9G | 2C,7G | 3C,3G | 0 | 0 | 3C,9H | — | 3C,8G | 0 | 2C,9G | 2C,9G | 10C | 2C,9G |
| Soybean | 8G | — | 9H | — | 0 | 4C,7G | 4G | 2C,8G | 0 | 9G | 9C | 10C | 7G |
| Rice | 10E | 2C,8G | 2C,9H | — | 5C,9H | 2C,9G | 3C,5H | 7G | 5C,6H | 3C,8G | 9C | 10C | 2G |
| Sorghum | 6C,9H | 2C | — | — | 10E | 9G | — | 2C,5H | — | 3U,9G | 3C,9G | 2U,9G | 3C,3H |
| Wheat | 2G | 1C | — | — | — | — | — | — | — | — | — | — | — |
| Cotton | 2H | 1C,3G | 2C,8H | 1C,2H | — | 3C,9H | 2C,5H | — | — | — | — | — | — |

TABLE A-continued

| | | | | | | | | | | | | | | | | | | | |
|---|---|---|---|---|---|---|---|---|---|---|---|---|---|---|---|---|---|---|---|
| Soybean | 2C,3G | 1C,3G | 2C,5H | 1C,2G | | 2C,3H | 1H | 3C,6H | 1C,2G | 3C,3H | 2C,3G | 2C,8G | 3C,5H | 3C,9G | 3C,5G | 5C,9G | 2C,3H | 3C,8G | 2H,4G |
| Rice | 4C,9G | 3C,9G | 4C,9G | 3C,9G | 2G | 5C,9G | 2C,8G | 5C,9G | 5C,9G | 3C,8G | 2C,5G | 3C,9G | 5C,9G | 5C,9G | 5C,9G | 5C,9G | 6C,9G | 4C,8G | 3C,7G |
| Sorghum | 3C,9G | 3C,9H | 2C,9H | 3C,9H | 3G | 4C,9H | 4C,9H | 2C,9G | 4C,4H | 3C,9G | 3C,9H | 2U,9G | 9G | 3C,9G | 6C,9G | 6C,9G | 9G | 2C,2H | 2G |
| Sugar beet | 2C,3G | 2C,5G | 0 | 9C | 0 | 3C,5H | 3C,6G | 3C,5H | 4C,4H | 1C | 3C,3H | 9C | 3C,7G | 5C,9G | 3C,8G | 3C,7G | 2C,6H | 2C,6G | 1C |

PRE-EMERGENCE

| | | | | | | | | | | | | | | | | | | | |
|---|---|---|---|---|---|---|---|---|---|---|---|---|---|---|---|---|---|---|---|
| Morningglory | 2C | 3C,5G | 9G | 2C,5G | 1C | 3H | 2C,3H | 6H | 8H | 2C,7H | 9C | 9H | 3C,5H | 9G | 2C | 9C | 9G | 2C | 2G |
| Cocklebur | 1H | 9H | 9H | 9H | 0 | 8H | 0 | 0 | 7H | 2G | 9H | 9H | 8H | 8H | 9H | 9H | 3H | 0 | 0 |
| Sicklepod | 3H | 2C,3G | 2C,5G | 0 | 1C | 3C | 1C | 0 | 5C,8G | 0 | 3C,9G | 3C,9G | 3C,3H | 8G | 5G | 9C | — | — | 0 |
| Nutsedge | 0 | 5G | 3C,6G | 2C | 0 | 3G | 0 | 0 | 2G | 0 | 3G | 2U,9G | 0 | 5G | 3G | 8G | 0 | 0 | 0 |
| Crabgrass | 2G | 5G,2C | 3C,6G | 3C,6G | 0 | 5G | 3G | 2G | 2C,3G | 2G | 5G | 3G | 2G | 3C,9G | 3C,9G | 5C,9G | 1C | 2G | 0 |
| Barnyardgrass | 2C,8H | 3C,9H | 9H | 3C,6G | 0 | 3C,9H | 2H | 2G | 3G,5C | 0 | 3C,7H | 3C,9H | 3C,7H | 5C,9G | 3C,7H | 5C,9H | 3C,8H | 3C,6G | 1H |
| Wild Oats | 2C,8H | 3C,9G | 5C,9H | 2C,6G | 0 | 4C,9G | 2C | 2C,4G | 3C,9G | 2G | 3C,8G | 3C,9H | 3C,8G | 6C,9G | 4C,9H | 6C,9H | 2C,9H | 3C,7G | 1H |
| Wheat | 5G | 2C,9G | 9H | 6G | 0 | 2C,9G | 3G | 6G | 3C,9G | 0 | 3C,8G | 5C,9H | 3C,8G | 6C,9G | 5C,9G | 7C,9H | 2C,8G | 3C,9G | 2C |
| Corn | 4G | 2C,9H | 9G | 3C,8H | 0 | 2C,9H | 3C,8H | 3C,8H | 3C,9H | 4C,7G | 3C,9H | 9G | 8G | 6C,9H | 4C,9H | 1C,3G | 10E | 2C,2H | 0 |
| Soybean | 0 | 0 | 2C,2H | 1C | 1C | 2C,2H | 2C | 3C,8H | 3C,4H | 1C | 3C,4H | 3H | 1H | 3C,4H | 1G | 10E | 10E | 5C,9H | 2C |
| Rice | 2C,8H | 3C,7H | 10E | 5C,9G | 2C | 10H | 2C,8G | 3C,8H | 4C,9H | 5G | 4C,9H | 10E | 5C,9H | 10E | 10E | 10E | 3C,9G | 4C,9G | 2C |
| Sorghum | 3C,8H | 3C,9H | 5C,9H | 1C,9G | 2C,4G | 4C,9H | 3C,8H | 3C,8H | 4C,9H | 2C,8G | 4C,9H | 5C,9H | 3C,9G | 5C,9H | 5C,9H | 3C,9G | 2C,8G | 0 | 2H |
| Sugar beet | 3C,8G | 9G | 8G | 2C,9G | 6G | 9C | 0 | 0 | 4C,8H | 1C | 2C,7G | 9C | 2C,7G | 10C | 4C,9G | 2C,8G | 2C,8G | 2G | 3G |
| Cotton | — | — | — | — | — | 8G | 2G | 0 | 3C,3H | 1C | 6G,2C | 9G | 9G | 3C,9G | 9G | 9G | 2C,7G | 2G | 1C |

TEST B

Two plastic bulb pans were filled with fertilized and limed Woodstown sandy loam. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B.

cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (*Digitaria* spp.), nutsedge (*Cyperus rotundus*), barnyardgrass (*Echinochloa crusgalli*), giant foxtail (*Setaria faberii*), and wild oats (*Avena fatua*). The following species were grown in soil in a paper cup (12 cm diameter by 13 cm deep): sunflower, sugar beets and mustard. All plants were sprayed approximately 14 days after planting. Additional plant species are sometimes added to this standard test in order to evaluate unusual selectivity.

TABLE C

| Over-the-Top Soil/Foliage Treatment | |
|---|---|
| Rate kg/ha | Compound 1<br>0.015 |
| Soybeans | 9G,4C |
| Velvetleaf | 4G |
| Sesbania | 9G |
| Sicklepod | 8G |
| Cotton | 9G |
| Morningglory | 7G,4C |
| Alfalfa | 3G |
| Jimsonweed | 6G |
| Cocklebur | 4G |
| Corn | 9G,8C |
| Crabgrass | 9G |
| Rice | 9G,7C |

TABLE B

PRE-EMERGENCE ON WOODSTOWN SANDY LOAM

| | Compound No. | | | | | | | | | | |
|---|---|---|---|---|---|---|---|---|---|---|---|
| | 1 | | | 5 | | | | 4 | | 6 | |
| kg/ha | .015 | .060 | .250 | .015 | .030 | .120 | .250 | .030 | .120 | .030 | .120 |
| Crabgrass | 7G | 8G,3H | 9G,9C | 0 | 0 | 6G | 7G | 4G | 8G,5H | 0 | 0 |
| Barnyardgrass | 4G,3C | 6G | 9G,9C | 3G | 3G | 7G | 8G | 2G | 5G,2H | 5G | 7G |
| Sorghum | 7G,5H | 10C | 10C | 5G | 7G | 9G | 10C | — | — | 7G | 9G |
| Wild Oats | 2G | 7G,5H | 7G,5H | 3G | 4G | 8G | 9G | 0 | 5G | 2G | 6G |
| Johnsongrass | 5G,3H | 9G,8C | 9G,9C | 5G | 6G | 8G | 9G | 4G | 6G,5H | 4G | 8G |
| Dallisgrass | 3G | 5G | 7G | 0 | 6G | 6G | 8G | 5G | 8G,3H | 2G | 7G |
| Giant Foxtail | 4G | 8G,3H | 10C | 2G | 3G | 8G | 9G | 3G | 8G,5H | 5G | 7G |
| Ky. Bluegrass | — | 9G,9C | 10E | 7G | 8G | 9G | 9G,9C | 7G,3H | 9G,8C | 3G | 8G |
| Cheatgrass | 10E | 10C | 10E | 5G | 7G | 9G | 9G | 0 | 6G | 7G | 9G |
| Sugar beets | 5G,3C | 8G,8C | 10E | 3G | 7G | 9G | 10C | 3G | 5G,2H | 7G | 10C |
| Corn | 3G | 7G,5H | 9G,9C | 0 | 0 | 5G,3H | 8G,7H | 0 | 7G,5H | 3G | 4G,2C |
| Mustard | 5G | 8G,8C | 10C | 6G | 6G | 9G | 9G | 6G,3H | 9G,5H | 9G | 9G |
| Cocklebur | 4G | 4G | 6G,5H | 3G | 7G | 7G | 9G | 0 | 3G | 6G | 8G |
| Pigweed | — | 10E | 10E | — | — | — | — | 10C | 10C | — | — |
| Nutsedge | 0 | 2G | 7G | 0 | 0 | 2G | 5G | 0 | 0 | 7G | 9G |
| Cotton | 0 | 3G | 7G,5H | 4G | 4G | 5G | 7G | 0 | 0 | 2G,2C | 2G,2C |
| Morningglory | 0 | 8G,7C | 8G,5C | 0 | 2G | 3G | 8G | 0 | 3G | 5G,3C | 5G,5C |
| Sicklepod | 0 | 7G | 8G,5C | 0 | 0 | 2G | 8G | 3G | 4G | 0 | 2G |
| Teaweed | 0 | 0 | 7G,3H | 0 | 2G | 7G | 8G | 0 | 0 | 0 | 0 |
| Velvetleaf | 0 | 5G,2H | 7G,5H | 0 | 0 | 5G | 7G | 0 | 3G | 7G | 8G |
| Jimsonweed | 2G | 6G | 7G | 0 | 3G | 7G | 9G | 0 | 3G | 7G | 9G |
| Soybean | 0 | 3G,2H | 6G,5H | 2G | 3G | 5G,5H | 6G,5H | 0 | 0 | 0 | 2G |
| Rice | 10C | 8G,8C | 10E | 6G | 7G | 8G | 10C | 6G,3H | 8G,9C | 7G | 8G |
| Wheat | 3G | 8G,5H | 10C | 2G | 3G | 6G | 8G | 0 | 7G,5C | 2G | 2G |

TEST C

The test chemicals, dissolved in a non-phytotoxic solvent, were applied in an overall spray to the foliage and surrounding soil of selected plant species. One day after treatment, plants were checked for rapid burn injury. Approximately fourteen days after treatment all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25

| | |
|---|---|
| Nutsedge | 0 |
| Barnyardgrass | 3G |
| Wheat | 8G,4C |
| Giant Foxtail | 10C |
| Wild Oats | 8G |
| Sorghum | 8G,2U |
| Bindweed | 0 |
| Johnsongrass | 10C |
| Sunflower | 7G,1H |
| Rape | 0 |
| Sugar beets | 4G |

What is claimed is:

1. A compound of the formula

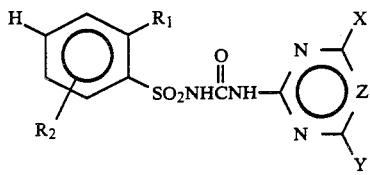

wherein $R_1$ is $S(O)_nR_3$;

$R_2$ is H, F, Cl, Br, $CH_3$, $OCH_3$, $CF_3$ or $NO_2$;

$R_3$ is $C_1$–$C_4$ alkyl, $C_3$–$C_4$ alkenyl or cyclopropylmethyl;

n is 0, 1 or 2;

X is $CH_3$, $C_2H_5$, $CH_3O$, $C_2H_5O$, $CH_2OCH_3$ or Cl;

Y is Cl, F, Br, $NH_2$, $NHCH_3$ or $N(CH_3)_2$; and

Z is CH;

and their agriculturally suitable salts; provided that (1) when $R_3$ is $C_3$–$C_4$ alkenyl, then Y is $NH_2$, $NHCH_3$ or $N(CH_3)_2$;

(2) when $R_3$ is $C_1$–$C_2$ alkyl and Y is Cl or Br, then X is other than $CH_3$ or $OCH_3$;

(3) when $R_3$ is $C_1$–$C_2$ alkyl and Y is $NH_2$ or $NHCH_3$, then X is other than Cl, $CH_2CH_3$ or $CH_2OCH_3$;

(4) when Y is Cl, F or Br, then X is $CH_3$, $OCH_3$ or $OCH_2CH_3$; and (5) when X is Cl, then Y is $N(CH_3)_2$.

2. Compounds of claim 1 where n is 2.

3. Compounds of claim 2 wherein $R_2$ is H, Cl, $CH_3$, $CH_3O$ or $CF_3$.

4. Compounds of claim 3 where X is $CH_3$ or $OCH_3$.

5. Compounds of claim 4 where $R_2$ is H.

6. The compound of claim 1 which is N-[(4-chloro-6-ethoxypyrimidin-2-yl)aminocarbonyl]-2-(propylsulfonyl)benzenesulfonamide.

7. The compound of claim 1 which is N-[(4-chloro-6-methoxypyrimidin-2-yl)aminocarbonyl]-2-(propylsulfonyl)benzenesulfonamide.

8. A composition suitable for controlling the growth of undesired vegetation which comprises an effective amount of a compound of claim 1 and at least one of the following: surfactant, solid or liquid diluent.

9. A composition suitable for controlling the growth of undesired vegetation which comprises an effective amount of a compound of claim 2 and at least one of the following: surfactant, solid or liquid diluent.

10. A composition suitable for controlling the growth of undesired vegetation which comprises an effective amount of a compound of claim 3 and at least one of the following: surfactant, solid or liquid diluent.

11. A composition suitable for controlling the growth of undesired vegetation which comprises an effective amount of a compound of claim 4 and at least one of the following: surfactant, solid or liquid diluent.

12. A composition suitable for controlling the growth of undesired vegetation which comprises an effective amount of a compound of claim 5 and at least one of the following: surfactant, solid or liquid diluent.

13. A composition suitable for controlling the growth of undesired vegetation which comprises an effective amount of the compound of claim 6 and at least one of the following: surfactant, solid or liquid diluent.

14. A method for controlling the growth of undesired vegetation which comprises applying to the locus to be protected an effective amount of a compound of claim 1.

15. A method for controlling the growth of undesired vegetation which comprises applying to the locus to be protected an effective amount of a compound of claim 2.

16. A method for controlling the growth of undesirred vegetation which comprises applying to the locus to be protected an effective amount of a compound of claim 3.

17. A method for controlling the growth of undesired vegetation which comprises applying to the locus to be protected an effective amount of a compound of claim 4.

18. A method for controlling the growth of undesired vegetation which comprises applying to the locus to be protected an effective amount of a compound of claim 5.

19. A method for controlling the growth of undesired vegetation which comprises applying to the locus to be protected an effective amount of the compound of claim 6.

* * * * *